US012637706B2

(12) United States Patent
Gohil et al.

(10) Patent No.: US 12,637,706 B2
(45) Date of Patent: May 26, 2026

(54) METHODS AND COMPOSITIONS RELATED TO MICROSPHERE SURFACE GELATION

(71) Applicant: 10x Genomics, Inc., Pleasanton, CA (US)

(72) Inventors: Shalini Gohil, Castro Valley, CA (US); Shea Thompson Lance, Livermore, CA (US); Geoffrey P. McDermott, Alfredton (AU); David Michael Patterson, Oakland, CA (US); Andrew D. Price, San Diego, CA (US)

(73) Assignee: 10x Genomics, Inc.

( * ) Notice: Subject to any disclaimer, the term of this patent is extended or adjusted under 35 U.S.C. 154(b) by 735 days.

(21) Appl. No.: 18/187,981

(22) Filed: Mar. 22, 2023

(65) Prior Publication Data

US 2023/0304072 A1     Sep. 28, 2023

Related U.S. Application Data

(60) Provisional application No. 63/323,049, filed on Mar. 23, 2022.

(51) Int. Cl.
| | |
|---|---|
| *C12Q 1/6806* | (2018.01) |
| *B01J 13/02* | (2006.01) |
| *C08J 3/075* | (2006.01) |
| *C12N 15/10* | (2006.01) |

(52) U.S. Cl.
CPC ........... *C12Q 1/6806* (2013.01); *B01J 13/02* (2013.01); *C08J 3/075* (2013.01); *C12N 15/1082* (2013.01); *C08J 2333/26* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |

(Continued)

FOREIGN PATENT DOCUMENTS

| | | |
|---|---|---|
| CN | 1680604 | 10/2005 |
| EP | 1923471 | 5/2008 |

(Continued)

OTHER PUBLICATIONS

Kishi et al., "Light-Seq: light-directed in situ barcoding of biomolecules in fixed cells and tissues for spatially indexed sequencing," Nature Methods, Oct. 10, 2022, 19(11):1393-1402.

(Continued)

*Primary Examiner* — Sanza L. McClendon
(74) *Attorney, Agent, or Firm* — Fish & Richardson P.C.

(57) ABSTRACT

The present disclosure relates generally to compositions and methods for generating hydrogel coatings on features. In some embodiments, hydrogel-coated features are prepared by horseradish peroxidase-mediated gelation of microspheres. Some embodiments relate to methods for generating hydrogel coatings using particle templated emulsification. The disclosure also relates to the use of hydrogel-coated features in arrays for spatial analysis of biological analytes in biological samples.

22 Claims, 3 Drawing Sheets

(56)                  References Cited

U.S. PATENT DOCUMENTS

| | | | |
|---|---|---|---|
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,641,658 A | 6/1997 | Adams | |
| 5,648,245 A | 7/1997 | Fire et al. | |
| 5,658,751 A | 8/1997 | Yue | |
| 5,750,341 A | 5/1998 | Macevicz | |
| 5,763,175 A | 6/1998 | Brenner | |
| 5,830,711 A | 11/1998 | Barany et al. | |
| 5,837,832 A | 11/1998 | Chee et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 6,013,440 A | 1/2000 | Lipshutz | |
| 6,027,889 A | 2/2000 | Barany et al. | |
| 6,060,240 A | 5/2000 | Kamb et al. | |
| 6,130,073 A | 10/2000 | Eggerding | |
| 6,136,592 A | 10/2000 | Leighton | |
| 6,143,496 A | 11/2000 | Brown | |
| 6,153,389 A | 11/2000 | Haarer | |
| 6,165,714 A | 12/2000 | Lane et al. | |
| 6,172,218 B1 | 1/2001 | Brenner | |
| 6,210,891 B1 | 4/2001 | Nyren | |
| 6,210,894 B1 | 4/2001 | Brennan | |
| 6,214,587 B1 | 4/2001 | Dattagupta | |
| 6,258,568 B1 | 7/2001 | Nyren | |
| 6,266,459 B1 | 7/2001 | Walt | |
| 6,274,320 B1 | 8/2001 | Rothberg | |
| 6,300,063 B1 | 10/2001 | Lipshutz et al. | |
| 6,309,824 B1 | 10/2001 | Drmanac | |
| 6,344,316 B1 | 2/2002 | Lockhart | |
| 6,355,431 B1 | 3/2002 | Chee | |
| 6,368,801 B1 | 4/2002 | Faruqi | |
| 6,391,937 B1 | 5/2002 | Beuhler et al. | |
| 6,401,267 B1 | 6/2002 | Drmanac | |
| 6,404,907 B1 | 6/2002 | Gilchrist | |
| 6,432,360 B1 | 8/2002 | Church et al. | |
| 6,503,713 B1 | 1/2003 | Rana | |
| 6,506,561 B1 | 1/2003 | Cheval et al. | |
| 6,544,732 B1 | 4/2003 | Chee | |
| 6,565,727 B1 | 5/2003 | Shenderov | |
| 6,620,584 B1 | 9/2003 | Chee | |
| 6,632,641 B1 | 10/2003 | Brennan | |
| 6,737,236 B1 | 5/2004 | Pieken et al. | |
| 6,770,441 B2 | 8/2004 | Dickinson | |
| 6,773,886 B2 | 8/2004 | Kaufman | |
| 6,787,308 B2 | 9/2004 | Balasubramanian | |
| 6,800,453 B2 | 10/2004 | Labaer | |
| 6,812,005 B2 | 11/2004 | Fan et al. | |
| 6,828,100 B1 | 12/2004 | Ronaghi | |
| 6,833,246 B2 | 12/2004 | Balasubramanian | |
| 6,859,570 B2 | 2/2005 | Walt | |
| 6,864,052 B1 | 3/2005 | Drmanac | |
| 6,897,023 B2 | 5/2005 | Fu | |
| 6,911,132 B2 | 6/2005 | Pamula | |
| 6,942,968 B1 | 9/2005 | Dickinson et al. | |
| 6,969,488 B2 | 11/2005 | Bridgham | |
| 6,977,033 B2 | 12/2005 | Becker | |
| 7,052,244 B2 | 5/2006 | Fouillet | |
| 7,057,026 B2 | 6/2006 | Barnes | |
| 7,115,400 B1 | 10/2006 | Adessi | |
| 7,118,883 B2 | 10/2006 | Inoue | |
| 7,163,612 B2 | 1/2007 | Sterling | |
| 7,166,431 B2 | 1/2007 | Chee et al. | |
| 7,211,414 B2 | 5/2007 | Hardin | |
| 7,255,994 B2 | 8/2007 | Lao | |
| 7,258,976 B2 | 8/2007 | Mitsuhashi | |
| 7,262,063 B2 * | 8/2007 | Banerjee | C08J 3/075 |
| | | | 428/323 |
| 7,297,518 B2 | 11/2007 | Quake | |
| 7,315,019 B2 | 1/2008 | Turner | |
| 7,329,492 B2 | 2/2008 | Hardin | |
| 7,361,488 B2 | 4/2008 | Fan et al. | |
| 7,378,242 B2 | 5/2008 | Hurt | |
| 7,393,665 B2 | 7/2008 | Brenner | |
| 7,405,281 B2 | 7/2008 | Xu | |
| 7,407,757 B2 | 8/2008 | Brenner | |
| 7,537,897 B2 | 5/2009 | Brenner | |
| 7,544,473 B2 | 6/2009 | Brennan | |
| 7,563,576 B2 | 7/2009 | Chee | |
| 7,582,420 B2 | 9/2009 | Oliphant et al. | |
| 7,601,498 B2 | 10/2009 | Mao | |
| 7,625,765 B2 * | 12/2009 | Banerjee | C12Q 1/6837 |
| | | | 428/323 |
| 7,635,566 B2 | 12/2009 | Brenner | |
| 7,641,779 B2 | 1/2010 | Becker | |
| 7,674,752 B2 | 3/2010 | He | |
| 7,776,567 B2 | 8/2010 | Mao | |
| 7,803,943 B2 | 9/2010 | Mao | |
| 7,858,321 B2 | 12/2010 | Glezer | |
| 7,910,304 B2 | 3/2011 | Drmanac | |
| 7,955,794 B2 | 6/2011 | Shen et al. | |
| 7,960,119 B2 | 6/2011 | Chee | |
| 8,003,354 B2 | 8/2011 | Shen et al. | |
| 8,148,068 B2 | 4/2012 | Brenner | |
| 8,206,917 B2 | 6/2012 | Chee | |
| 8,288,103 B2 | 10/2012 | Oliphant | |
| 8,460,865 B2 | 6/2013 | Chee | |
| 8,481,257 B2 | 7/2013 | Van Eijk | |
| 8,603,743 B2 | 12/2013 | Liu et al. | |
| 8,815,512 B2 | 8/2014 | Van Eijk | |
| 8,835,358 B2 | 9/2014 | Fodor | |
| 8,911,945 B2 | 12/2014 | Van Eijk | |
| 9,062,348 B1 | 6/2015 | Van Eijk | |
| 9,085,798 B2 | 7/2015 | Chee | |
| 9,194,001 B2 | 11/2015 | Brenner | |
| 9,217,176 B2 | 12/2015 | Faham | |
| 9,290,808 B2 | 3/2016 | Fodor | |
| 9,290,809 B2 | 3/2016 | Fodor | |
| 9,328,383 B2 | 5/2016 | Van Eijk | |
| 9,330,295 B2 | 5/2016 | Dunn | |
| 9,334,536 B2 | 5/2016 | Van Eijk | |
| 9,371,598 B2 | 6/2016 | Chee | |
| 9,436,088 B2 * | 9/2016 | Seul | G03F 7/164 |
| 9,506,061 B2 | 11/2016 | Brown et al. | |
| 9,512,487 B2 | 12/2016 | Faham et al. | |
| 9,593,365 B2 | 3/2017 | Frisen et al. | |
| 9,644,204 B2 | 5/2017 | Hindson et al. | |
| 9,694,361 B2 | 7/2017 | Bharadwaj | |
| 9,702,004 B2 | 7/2017 | Van Eijk | |
| 9,727,810 B2 | 8/2017 | Fodor et al. | |
| 9,777,324 B2 | 10/2017 | Van Eijk | |
| 9,834,814 B2 | 12/2017 | Peter et al. | |
| 9,850,536 B2 | 12/2017 | Oliphant et al. | |
| 9,868,979 B2 | 1/2018 | Chee et al. | |
| 9,879,313 B2 | 1/2018 | Chee et al. | |
| 10,002,316 B2 | 6/2018 | Fodor et al. | |
| 10,011,872 B1 | 7/2018 | Belgrader et al. | |
| 10,023,907 B2 | 7/2018 | Van Eijk | |
| 10,030,261 B2 | 7/2018 | Frisen et al. | |
| 10,066,265 B2 | 9/2018 | Klinger et al. | |
| 10,077,478 B2 | 9/2018 | Faham et al. | |
| 10,168,328 B2 | 1/2019 | Berka | |
| 10,273,541 B2 | 4/2019 | Hindson et al. | |
| 10,308,982 B2 | 6/2019 | Chee | |
| 10,357,771 B2 | 7/2019 | Bharadwaj | |
| 10,392,663 B2 | 8/2019 | Emerson et al. | |
| 10,428,325 B1 | 10/2019 | Klinger | |
| 10,472,669 B2 | 11/2019 | Chee | |
| 10,480,022 B2 | 11/2019 | Chee | |
| 10,480,029 B2 | 11/2019 | Bent et al. | |
| 10,494,667 B2 | 12/2019 | Chee | |
| 10,550,429 B2 | 2/2020 | Harada et al. | |

(56)　　　　　References Cited

U.S. PATENT DOCUMENTS

| | | | |
|---|---|---|---|
| 10,590,244 | B2 | 3/2020 | Delaney et al. |
| 10,662,468 | B2 | 5/2020 | Chee |
| 10,724,078 | B2 | 7/2020 | Van Driel et al. |
| 10,725,027 | B2 | 7/2020 | Bell |
| 10,774,372 | B2 | 9/2020 | Chee et al. |
| 10,774,374 | B2 | 9/2020 | Frisen et al. |
| 10,787,701 | B2 | 9/2020 | Chee |
| 10,858,702 | B2 | 12/2020 | Lucero et al. |
| 10,913,975 | B2 | 2/2021 | So et al. |
| 10,914,730 | B2 | 2/2021 | Chee et al. |
| 10,927,403 | B2 | 2/2021 | Chee et al. |
| 10,961,566 | B2 | 3/2021 | Chee |
| 10,995,362 | B2 | 5/2021 | Dallett et al. |
| 11,001,879 | B1 | 5/2021 | Chee |
| 11,008,607 | B2 | 5/2021 | Chee |
| 11,046,996 | B1 | 6/2021 | Chee et al. |
| 11,067,567 | B2 | 7/2021 | Chee |
| 11,156,603 | B2 | 10/2021 | Chee |
| 11,162,132 | B2 | 11/2021 | Frisen et al. |
| 11,208,684 | B2 | 12/2021 | Chee |
| 11,214,796 | B2 | 1/2022 | Shirai et al. |
| 11,286,515 | B2 | 3/2022 | Chee et al. |
| 11,293,917 | B2 | 4/2022 | Chee |
| 11,299,774 | B2 | 4/2022 | Frisen et al. |
| 11,313,856 | B2 | 4/2022 | Chee |
| 11,332,790 | B2 | 5/2022 | Chell et al. |
| 11,352,659 | B2 | 6/2022 | Frisen et al. |
| 11,352,667 | B2 | 6/2022 | Hauling et al. |
| 11,359,228 | B2 | 6/2022 | Chee et al. |
| 11,365,442 | B2 | 6/2022 | Chee |
| 11,371,086 | B2 | 6/2022 | Chee |
| 11,384,386 | B2 | 7/2022 | Chee |
| 11,390,912 | B2 | 7/2022 | Frisen et al. |
| 11,401,545 | B2 | 8/2022 | Chee |
| 11,407,992 | B2 | 8/2022 | Dadhwal |
| 11,408,029 | B2 | 8/2022 | Katiraee et al. |
| 11,434,524 | B2 | 9/2022 | Ramachandran Iyer et al. |
| 11,459,607 | B1 | 10/2022 | Terry et al. |
| 11,479,809 | B2 | 10/2022 | Frisen et al. |
| 11,479,810 | B1 | 10/2022 | Chee |
| 11,492,612 | B1 | 11/2022 | Dadhwal |
| 11,501,440 | B2 | 11/2022 | Weisenfeld et al. |
| 11,505,828 | B2 | 11/2022 | Chell et al. |
| 11,512,308 | B2 | 11/2022 | Gallant et al. |
| 11,519,022 | B2 | 12/2022 | Chee |
| 11,519,033 | B2 | 12/2022 | Schnall-Levin et al. |
| 11,530,438 | B2 | 12/2022 | Persson et al. |
| 11,535,887 | B2 | 12/2022 | Gallant et al. |
| 11,542,543 | B2 | 1/2023 | Chee |
| 11,549,138 | B2 | 1/2023 | Chee |
| 11,560,587 | B2 | 1/2023 | Chee |
| 11,560,592 | B2 | 1/2023 | Chew et al. |
| 11,560,593 | B2 | 1/2023 | Chell et al. |
| 11,592,447 | B2 | 2/2023 | Uytingco et al. |
| 11,608,498 | B2 | 3/2023 | Gallant et al. |
| 11,608,520 | B2 | 3/2023 | Galonska et al. |
| 11,613,773 | B2 | 3/2023 | Frisen et al. |
| 11,618,897 | B2 | 4/2023 | Kim et al. |
| 11,618,918 | B2 | 4/2023 | Chee et al. |
| 11,624,063 | B2 | 4/2023 | Dadhwal |
| 11,624,086 | B2 | 4/2023 | Uytingco et al. |
| 11,634,756 | B2 | 4/2023 | Chee |
| 11,649,485 | B2 | 5/2023 | Yin et al. |
| 11,661,626 | B2 | 5/2023 | Katiraee et al. |
| 11,680,260 | B2 | 6/2023 | Kim et al. |
| 11,692,218 | B2 | 7/2023 | Engblom et al. |
| 11,702,693 | B2 | 7/2023 | Bharadwaj |
| 11,702,698 | B2 | 7/2023 | Stoeckius |
| 11,713,480 | B2 | 8/2023 | Lee |
| 11,732,292 | B2 | 8/2023 | Chee |
| 11,732,299 | B2 | 8/2023 | Ramachandran Iyer |
| 11,732,300 | B2 | 8/2023 | Bava |
| 11,733,238 | B2 | 8/2023 | Chee |
| 11,739,372 | B2 | 8/2023 | Frisen et al. |
| 11,739,381 | B2 | 8/2023 | Chew et al. |
| 11,753,673 | B2 | 9/2023 | Chew et al. |
| 11,753,674 | B2 | 9/2023 | Chee et al. |
| 11,753,675 | B2 | 9/2023 | Ramachandran Iyer |
| 11,761,030 | B2 | 9/2023 | Chee |
| 11,761,038 | B1 | 9/2023 | Stoeckius |
| 11,767,550 | B2 | 9/2023 | Chee |
| 11,768,175 | B1 | 9/2023 | Kim et al. |
| 11,773,433 | B2 | 10/2023 | Gallant et al. |
| 11,781,130 | B2 | 10/2023 | Dadhwal |
| 11,788,122 | B2 | 10/2023 | Frisen et al. |
| 11,795,498 | B2 | 10/2023 | Frisen et al. |
| 11,795,507 | B2 | 10/2023 | Chell et al. |
| 11,808,769 | B2 | 11/2023 | Uytingco et al. |
| 11,821,024 | B2 | 11/2023 | Chee et al. |
| 11,821,035 | B1 | 11/2023 | Bent et al. |
| 11,827,935 | B1 | 11/2023 | Ramachandran Iyer et al. |
| 11,835,462 | B2 | 12/2023 | Bava |
| 11,840,687 | B2 | 12/2023 | Gallant et al. |
| 11,840,724 | B2 | 12/2023 | Chew et al. |
| 11,845,979 | B2 | 12/2023 | Engblom et al. |
| 11,859,178 | B2 | 1/2024 | Gallant et al. |
| 11,866,767 | B2 | 1/2024 | Uytingco et al. |
| 11,866,770 | B2 | 1/2024 | Chee |
| 11,873,482 | B2 | 1/2024 | Kim et al. |
| 11,891,654 | B2 | 2/2024 | Alvarado Martinez et al. |
| 11,898,205 | B2 | 2/2024 | Bava |
| 11,926,822 | B1 | 3/2024 | Gohil et al. |
| 11,926,863 | B1 | 3/2024 | Boutet |
| 11,926,867 | B2 | 3/2024 | Yin et al. |
| 11,933,957 | B1 | 3/2024 | Tentori et al. |
| 11,952,627 | B2 | 4/2024 | Stoeckius |
| 11,959,076 | B2 | 4/2024 | Kim et al. |
| 11,959,130 | B2 | 4/2024 | Galonska et al. |
| 11,965,213 | B2 | 4/2024 | Williams |
| 11,970,739 | B2 | 4/2024 | Chew et al. |
| 11,981,958 | B1 | 5/2024 | Galonska |
| 11,981,960 | B1 | 5/2024 | Lin et al. |
| 11,981,965 | B2 | 5/2024 | Chell et al. |
| RE50,065 | E | 7/2024 | Frisen et al. |
| 12,024,741 | B2 | 7/2024 | Tentori et al. |
| 12,031,177 | B1 | 7/2024 | Tentori et al. |
| 12,060,604 | B2 | 8/2024 | Katiraee et al. |
| 12,071,655 | B2 | 8/2024 | Sukovich et al. |
| 12,076,701 | B2 | 9/2024 | Bava |
| 12,098,417 | B2 | 9/2024 | Engblom et al. |
| 12,098,985 | B2 | 9/2024 | Cox et al. |
| 12,110,541 | B2 | 10/2024 | Bava |
| 12,117,439 | B2 | 10/2024 | Delaney et al. |
| 12,128,403 | B2 | 10/2024 | Kim et al. |
| 12,129,516 | B2 | 10/2024 | Tentori et al. |
| 12,157,124 | B2 | 12/2024 | Cox et al. |
| 12,180,543 | B2 | 12/2024 | Uytingco et al. |
| 12,195,790 | B2 | 1/2025 | Sukovich et al. |
| 12,203,134 | B2 | 1/2025 | Nagendran et al. |
| 12,209,280 | B1 | 1/2025 | Mignardi et al. |
| 12,223,751 | B2 | 2/2025 | Li et al. |
| 12,228,544 | B2 | 2/2025 | Kim et al. |
| 12,234,505 | B2 | 2/2025 | Chee |
| 12,241,060 | B2 | 3/2025 | Kim et al. |
| 12,241,890 | B2 | 3/2025 | Delaney et al. |
| 12,249,085 | B2 | 3/2025 | Tentori et al. |
| 12,265,079 | B1 | 4/2025 | Bent |
| 12,270,077 | B2 | 4/2025 | Schnall-Levin et al. |
| 12,275,988 | B2 | 4/2025 | Galonska et al. |
| 12,281,357 | B1 | 4/2025 | Tentori et al. |
| 12,286,673 | B2 | 4/2025 | Bava |
| 12,287,264 | B2 | 4/2025 | Cox et al. |
| 12,297,486 | B2 | 5/2025 | Patterson et al. |
| 12,297,487 | B2 | 5/2025 | Chee |
| 12,297,488 | B2 | 5/2025 | Chee |
| 12,344,892 | B2 | 7/2025 | Schnall-Levin et al. |
| 12,365,935 | B2 | 7/2025 | Chew et al. |
| 12,365,942 | B2 | 7/2025 | Stocckius |
| 12,371,688 | B2 | 7/2025 | Kim et al. |
| 12,378,607 | B2 | 8/2025 | Schnall-Levin et al. |
| 12,385,083 | B2 | 8/2025 | Shah |
| 12,391,979 | B2 | 8/2025 | Chee |
| 12,391,980 | B2 | 8/2025 | Chee |
| 12,399,123 | B1 | 8/2025 | Shah et al. |

(56) References Cited

U.S. PATENT DOCUMENTS

| | | | |
|---|---|---|---|
| 12,404,544 | B2 | 9/2025 | Tentori et al. |
| 12,405,264 | B2 | 9/2025 | Stoeckius |
| 12,416,603 | B2 | 9/2025 | Tentori et al. |
| 12,435,363 | B1 | 10/2025 | Gallant et al. |
| 12,442,045 | B2 | 10/2025 | Williams |
| 12,497,654 | B2 | 12/2025 | Ramachandran Iyer et al. |
| 12,508,590 | B2 | 12/2025 | Kim et al. |
| D1,108,656 | S | 1/2026 | Alimsijah et al. |
| 12,529,094 | B2 | 1/2026 | Bent et al. |
| 12,545,949 | B2 | 2/2026 | Bent et al. |
| 12,553,805 | B2 | 2/2026 | Shahjamali |
| 12,553,898 | B1 | 2/2026 | Uytingco et al. |
| 12,566,113 | B2 * | 3/2026 | Delaney ............... G01N 1/30 |
| 12,566,114 | B2 | 3/2026 | Cox et al. |
| 12,571,029 | B1 | 3/2026 | Galonska et al. |
| 2002/0040275 | A1 | 4/2002 | Cravatt |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0113713 | A1 | 6/2003 | Glezer |
| 2003/0148335 | A1 | 8/2003 | Shen et al. |
| 2003/0162216 | A1 | 8/2003 | Gold |
| 2003/0205632 | A1 | 11/2003 | Kim et al. |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2004/0033499 | A1 | 2/2004 | Ilsley et al. |
| 2004/0067492 | A1 | 4/2004 | Peng et al. |
| 2004/0096853 | A1 | 5/2004 | Mayer |
| 2004/0106110 | A1 | 6/2004 | Balasubramanian |
| 2004/0112442 | A1 | 6/2004 | Maerkl |
| 2005/0019842 | A1 | 1/2005 | Prober et al. |
| 2005/0037393 | A1 | 2/2005 | Gunderson et al. |
| 2005/0048580 | A1 | 3/2005 | Labaer |
| 2005/0100900 | A1 | 5/2005 | Kawashima et al. |
| 2005/0130173 | A1 | 6/2005 | Leamon et al. |
| 2005/0130188 | A1 | 6/2005 | Walt |
| 2005/0136414 | A1 | 6/2005 | Gunderson et al. |
| 2005/0170373 | A1 | 8/2005 | Monforte |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0244850 | A1 | 11/2005 | Huang |
| 2005/0260653 | A1 | 11/2005 | LaBaer |
| 2006/0041385 | A1 | 2/2006 | Bauer et al. |
| 2006/0188906 | A1 | 8/2006 | Kim et al. |
| 2006/0194331 | A1 | 8/2006 | Pamula et al. |
| 2006/0211001 | A1 | 9/2006 | Yu et al. |
| 2006/0216775 | A1 | 9/2006 | Burkart et al. |
| 2006/0263789 | A1 | 11/2006 | Kincaid |
| 2006/0275782 | A1 | 12/2006 | Gunderson et al. |
| 2007/0020640 | A1 | 1/2007 | McCloskey et al. |
| 2007/0054288 | A1 | 3/2007 | Su et al. |
| 2007/0099208 | A1 | 5/2007 | Drmanac et al. |
| 2007/0128624 | A1 | 6/2007 | Gormley et al. |
| 2007/0128656 | A1 | 6/2007 | Agrawal |
| 2007/0172873 | A1 | 7/2007 | Brenner et al. |
| 2007/0207482 | A1 | 9/2007 | Church et al. |
| 2007/0254305 | A1 | 11/2007 | Paik et al. |
| 2007/0269805 | A1 | 11/2007 | Hogers |
| 2008/0009420 | A1 | 1/2008 | Schroth et al. |
| 2008/0032301 | A1 | 2/2008 | Rank et al. |
| 2008/0108804 | A1 | 5/2008 | Hayashizaki et al. |
| 2008/0124252 | A1 | 5/2008 | Marchand et al. |
| 2008/0128627 | A1 | 6/2008 | Lundquist et al. |
| 2008/0160580 | A1 | 7/2008 | Adessi et al. |
| 2008/0220434 | A1 | 9/2008 | Thomas |
| 2008/0261204 | A1 | 10/2008 | Lexow |
| 2008/0286795 | A1 | 11/2008 | Kawashima et al. |
| 2009/0005252 | A1 | 1/2009 | Drmanac et al. |
| 2009/0006002 | A1 | 1/2009 | Honisch et al. |
| 2009/0011943 | A1 | 1/2009 | Drmanac et al. |
| 2009/0018024 | A1 | 1/2009 | Church et al. |
| 2009/0026082 | A1 | 1/2009 | Rothberg et al. |
| 2009/0048510 | A1 | 2/2009 | Miller et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0155781 | A1 | 6/2009 | Drmanac et al. |
| 2009/0233802 | A1 | 9/2009 | Bignell et al. |
| 2009/0253581 | A1 | 10/2009 | van Eijk et al. |
| 2009/0270273 | A1 | 10/2009 | Burns et al. |
| 2009/0291854 | A1 | 11/2009 | Weisinger-Mayr et al. |
| 2009/0312193 | A1 | 12/2009 | Kim et al. |
| 2010/0035249 | A1 | 2/2010 | Hayashizaki et al. |
| 2010/0047790 | A1 | 2/2010 | Southern et al. |
| 2010/0069263 | A1 | 3/2010 | Shendure et al. |
| 2010/0120097 | A1 | 5/2010 | Matz et al. |
| 2010/0120098 | A1 | 5/2010 | Grunenwald et al. |
| 2010/0137143 | A1 | 6/2010 | Rothberg et al. |
| 2010/0145037 | A1 | 6/2010 | Brive et al. |
| 2010/0282617 | A1 | 11/2010 | Rothberg et al. |
| 2011/0028685 | A1 | 2/2011 | Purkayastha et al. |
| 2011/0048951 | A1 | 3/2011 | Wu |
| 2011/0059436 | A1 | 3/2011 | Hardin et al. |
| 2011/0059865 | A1 | 3/2011 | Smith et al. |
| 2011/0237449 | A1 | 9/2011 | McMaster et al. |
| 2011/0244448 | A1 | 10/2011 | Shirai et al. |
| 2011/0245111 | A1 | 10/2011 | Chee |
| 2012/0129248 | A1 | 5/2012 | Chee et al. |
| 2012/0135871 | A1 | 5/2012 | van Eijk et al. |
| 2012/0195810 | A1 | 8/2012 | Cohen et al. |
| 2012/0202698 | A1 | 8/2012 | van Eijk et al. |
| 2012/0270748 | A1 | 10/2012 | Chee et al. |
| 2013/0065788 | A1 | 3/2013 | Glezer et al. |
| 2013/0096033 | A1 | 4/2013 | Routenberg |
| 2013/0109595 | A1 | 5/2013 | Routenberg |
| 2014/0066318 | A1 | 3/2014 | Frisen et al. |
| 2014/0079923 | A1 | 3/2014 | George et al. |
| 2014/0243224 | A1 | 8/2014 | Barnard et al. |
| 2014/0270435 | A1 | 9/2014 | Dunn |
| 2014/0274731 | A1 | 9/2014 | Raymond et al. |
| 2014/0323330 | A1 | 10/2014 | Glezer et al. |
| 2014/0378350 | A1 | 12/2014 | Hindson et al. |
| 2015/0292988 | A1 | 10/2015 | Bharadwaj et al. |
| 2015/0344942 | A1 | 12/2015 | Frisen et al. |
| 2015/0376609 | A1 | 12/2015 | Hindson et al. |
| 2016/0032282 | A1 | 2/2016 | Vigneault et al. |
| 2016/0033496 | A1 | 2/2016 | Chou et al. |
| 2016/0138091 | A1 | 5/2016 | Chee et al. |
| 2016/0145677 | A1 | 5/2016 | Chee et al. |
| 2016/0253584 | A1 | 9/2016 | Fodor et al. |
| 2016/0289740 | A1 | 10/2016 | Fu et al. |
| 2016/0298180 | A1 | 10/2016 | Chee |
| 2016/0369066 | A1 * | 12/2016 | Seul .................... C12Q 1/6837 |
| 2017/0159109 | A1 | 6/2017 | Zheng et al. |
| 2017/0220733 | A1 | 8/2017 | Zhuang et al. |
| 2017/0342405 | A1 | 11/2017 | Fu et al. |
| 2018/0057873 | A1 | 3/2018 | Zhou et al. |
| 2018/0080078 | A1 | 3/2018 | Robins et al. |
| 2018/0088112 | A1 | 3/2018 | Fan et al. |
| 2018/0112212 | A1 | 4/2018 | Nicol et al. |
| 2018/0112261 | A1 | 4/2018 | Van Driel et al. |
| 2018/0180601 | A1 | 6/2018 | Pedersen et al. |
| 2018/0201980 | A1 | 7/2018 | Chee et al. |
| 2018/0216162 | A1 | 8/2018 | Belhocine et al. |
| 2018/0245142 | A1 | 8/2018 | So et al. |
| 2018/0291439 | A1 | 10/2018 | van Eijk et al. |
| 2018/0305681 | A1 | 10/2018 | Jovanovich et al. |
| 2018/0312822 | A1 | 11/2018 | Lee et al. |
| 2018/0356343 | A1 | 12/2018 | Neuman et al. |
| 2019/0064173 | A1 | 2/2019 | Bharadwaj et al. |
| 2019/0161796 | A1 | 5/2019 | Hauling et al. |
| 2019/0177777 | A1 | 6/2019 | Chee |
| 2019/0177778 | A1 | 6/2019 | Chee |
| 2019/0177789 | A1 | 6/2019 | Hindson et al. |
| 2019/0177800 | A1 | 6/2019 | Boutet et al. |
| 2019/0203275 | A1 | 7/2019 | Frisen et al. |
| 2019/0233878 | A1 | 8/2019 | Delaney et al. |
| 2019/0249226 | A1 | 8/2019 | Bent et al. |

(56) References Cited

U.S. PATENT DOCUMENTS

| | | |
|---|---|---|
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0064266 A1 | 2/2020 | Vieceli et al. |
| 2020/0071751 A1 | 3/2020 | Daugharthy et al. |
| 2020/0109443 A1 | 4/2020 | Chee |
| 2020/0131570 A1 | 4/2020 | Berti et al. |
| 2020/0173985 A1 | 6/2020 | Dong et al. |
| 2020/0256867 A1 | 8/2020 | Hennek et al. |
| 2020/0277663 A1 | 9/2020 | Iyer |
| 2020/0277664 A1 | 9/2020 | Frenz |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0277460 A1 | 9/2021 | Bava |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0308332 A1* | 10/2021 | Olsson .................... A61L 27/48 |
| 2021/0317198 A1 | 10/2021 | Croote et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0056435 A1* | 2/2022 | Agresti ............... C12Q 1/6853 |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0178810 A1* | 6/2022 | Kim .................. G01N 21/6428 |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0031305 A1 | 2/2023 | Hernandez Neuta et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |

(56) References Cited

U.S. PATENT DOCUMENTS

| | | | |
|---|---|---|---|
| 2023/0107023 A1 | 4/2023 | Chee | |
| 2023/0111225 A1 | 4/2023 | Chew et al. | |
| 2023/0113230 A1 | 4/2023 | Kim et al. | |
| 2023/0126825 A1 | 4/2023 | Nagendran et al. | |
| 2023/0129552 A1 | 4/2023 | Ramachandran Iyer | |
| 2023/0135010 A1 | 5/2023 | Tentori et al. | |
| 2023/0143569 A1 | 5/2023 | Iyer et al. | |
| 2023/0145575 A1 | 5/2023 | Gallant et al. | |
| 2023/0147726 A1 | 5/2023 | Hadrup et al. | |
| 2023/0151412 A1 | 5/2023 | Chee | |
| 2023/0159994 A1 | 5/2023 | Chee | |
| 2023/0159995 A1 | 5/2023 | Iyer et al. | |
| 2023/0160008 A1 | 5/2023 | Chell et al. | |
| 2023/0175045 A1 | 6/2023 | Katsori et al. | |
| 2023/0183684 A1 | 6/2023 | Gallant et al. | |
| 2023/0183785 A1 | 6/2023 | Frisen et al. | |
| 2023/0194469 A1 | 6/2023 | Tentori et al. | |
| 2023/0194470 A1 | 6/2023 | Kim et al. | |
| 2023/0203478 A1 | 6/2023 | Kim et al. | |
| 2023/0212650 A1 | 7/2023 | Chew et al. | |
| 2023/0212655 A1 | 7/2023 | Chee | |
| 2023/0212656 A1 | 7/2023 | Chow et al. | |
| 2023/0220368 A1 | 7/2023 | Kim | |
| 2023/0220454 A1 | 7/2023 | Bent et al. | |
| 2023/0220455 A1 | 7/2023 | Galonska et al. | |
| 2023/0227811 A1 | 7/2023 | Dadhwal | |
| 2023/0228762 A1 | 7/2023 | Uytingco et al. | |
| 2023/0242973 A1 | 8/2023 | Frisen et al. | |
| 2023/0242976 A1 | 8/2023 | Tentori et al. | |
| 2023/0265488 A1 | 8/2023 | Gohil et al. | |
| 2023/0265489 A1 | 8/2023 | Uytingco et al. | |
| 2023/0265491 A1 | 8/2023 | Tentori et al. | |
| 2023/0267625 A1 | 8/2023 | Tentori et al. | |
| 2023/0279474 A1 | 9/2023 | Katiraee | |
| 2023/0279477 A1 | 9/2023 | Kvastad et al. | |
| 2023/0279481 A1 | 9/2023 | Marrache et al. | |
| 2023/0287399 A1 | 9/2023 | Gallant et al. | |
| 2023/0287475 A1 | 9/2023 | Chell et al. | |
| 2023/0287481 A1 | 9/2023 | Katsori et al. | |
| 2023/0295699 A1 | 9/2023 | Sukovich et al. | |
| 2023/0295722 A1 | 9/2023 | Bharadwaj | |
| 2023/0304074 A1 | 9/2023 | Chee et al. | |
| 2023/0304078 A1 | 9/2023 | Frisen et al. | |
| 2023/0313279 A1 | 10/2023 | Giacomello et al. | |
| 2023/0323340 A1 | 10/2023 | Dadhwal | |
| 2023/0323434 A1 | 10/2023 | Yin et al. | |
| 2023/0323436 A1 | 10/2023 | Chee | |
| 2023/0323447 A1 | 10/2023 | Schnall-Levin et al. | |
| 2023/0323453 A1 | 10/2023 | Stoeckius | |
| 2023/0332138 A1 | 10/2023 | Kim et al. | |
| 2023/0332211 A1 | 10/2023 | Chee | |
| 2023/0332212 A1 | 10/2023 | Chew et al. | |
| 2023/0332227 A1 | 10/2023 | Ramachandran Iyer | |
| 2023/0332247 A1 | 10/2023 | Singh et al. | |
| 2023/0351619 A1 | 11/2023 | Tentori et al. | |
| 2023/0358733 A1 | 11/2023 | Chee | |
| 2023/0366008 A1 | 11/2023 | Chew et al. | |
| 2023/0383285 A1 | 11/2023 | Kim et al. | |
| 2023/0383344 A1 | 11/2023 | Stoeckius | |
| 2023/0392204 A1 | 12/2023 | Chell et al. | |
| 2023/0393071 A1 | 12/2023 | Bava | |
| 2023/0407404 A1 | 12/2023 | Baumgartner et al. | |
| 2023/0416807 A1 | 12/2023 | Chee | |
| 2023/0416808 A1 | 12/2023 | Sukovich et al. | |
| 2023/0416850 A1 | 12/2023 | Singh et al. | |
| 2024/0002931 A1 | 1/2024 | Bava | |
| 2024/0011081 A1 | 1/2024 | Chee | |
| 2024/0011090 A1 | 1/2024 | Chew et al. | |
| 2024/0018572 A1 | 1/2024 | Mignardi | |
| 2024/0018575 A1 | 1/2024 | Gallant et al. | |
| 2024/0018589 A1 | 1/2024 | Schnall-Levin et al. | |
| 2024/0026445 A1 | 1/2024 | Ramachandran Iyer et al. | |
| 2024/0033743 A1 | 2/2024 | Tentori et al. | |
| 2024/0035937 A1 | 2/2024 | Cox et al. | |
| 2024/0043908 A1 | 2/2024 | Chew et al. | |
| 2024/0043925 A1 | 2/2024 | Bent et al. | |
| 2024/0052343 A1 | 2/2024 | Gallant et al. | |
| 2024/0053351 A1 | 2/2024 | Uytingco et al. | |
| 2024/0060115 A1 | 2/2024 | Chee et al. | |
| 2024/0067953 A1 | 2/2024 | Mikkelsen et al. | |
| 2024/0068016 A1 | 2/2024 | Frisen et al. | |
| 2024/0068017 A1 | 2/2024 | Lundeberg et al. | |
| 2024/0076723 A1 | 3/2024 | Mignardi | |
| 2024/0080346 A1 | 3/2024 | Engblom et al. | |
| 2024/0084365 A1 | 3/2024 | Frisen et al. | |
| 2024/0084366 A1 | 3/2024 | Chee | |
| 2024/0084383 A1 | 3/2024 | Ramachandran Iyer et al. | |
| 2024/0093274 A1 | 3/2024 | Frisen et al. | |
| 2024/0093290 A1 | 3/2024 | Stahl et al. | |
| 2024/0110228 A1 | 4/2024 | Uytingco et al. | |
| 2024/0124933 A1 | 4/2024 | Chell et al. | |
| 2024/0125772 A1 | 4/2024 | Delaney et al. | |
| 2024/0141327 A1 | 5/2024 | Kim et al. | |
| 2024/0158838 A1 | 5/2024 | Alvarado Martinez et al. | |
| 2024/0175080 A1 | 5/2024 | Galonska et al. | |
| 2024/0182968 A1 | 6/2024 | Bava | |
| 2024/0191286 A1 | 6/2024 | Boutet et al. | |
| 2024/0200121 A1 | 6/2024 | Boutet | |
| 2024/0209425 A1 | 6/2024 | Yin et al. | |
| 2024/0218427 A1 | 7/2024 | Sukovich et al. | |
| 2024/0218432 A1 | 7/2024 | Mielinis | |
| 2024/0219701 A1 | 7/2024 | Tentori et al. | |
| 2024/0253036 A1 | 8/2024 | Kim et al. | |
| 2024/0263218 A1 | 8/2024 | Katiraee et al. | |
| 2024/0271190 A1 | 8/2024 | Stoeckius et al. | |
| 2024/0271195 A1 | 8/2024 | Mikhaiel et al. | |
| 2024/0279712 A1 | 8/2024 | Fan et al. | |
| 2024/0279747 A1 | 8/2024 | Williams | |
| 2024/0287600 A1 | 8/2024 | Iyer et al. | |
| 2024/0294971 A1 | 9/2024 | Galonska | |
| 2024/0294974 A1 | 9/2024 | Galonska et al. | |
| 2024/0294975 A1 | 9/2024 | Lin et al. | |
| 2024/0301488 A1 | 9/2024 | Stoeckius | |
| 2024/0301489 A1 | 9/2024 | Chew et al. | |
| 2024/0360494 A1 | 10/2024 | Costa et al. | |
| 2024/0368711 A1 | 11/2024 | Giacomello et al. | |
| 2024/0377297 A1 | 11/2024 | Cox et al. | |
| 2024/0385088 A1 | 11/2024 | Kim et al. | |
| 2024/0392349 A1 | 11/2024 | Frisen et al. | |
| 2024/0392351 A1 | 11/2024 | Chee | |
| 2024/0392352 A1 | 11/2024 | Stahl et al. | |
| 2024/0392353 A1 | 11/2024 | Engblom et al. | |
| 2024/0401109 A1 | 12/2024 | Kim et al. | |
| 2024/0401117 A1 | 12/2024 | Bava | |
| 2024/0401118 A1 | 12/2024 | Tentori et al. | |
| 2024/0404301 A1 | 12/2024 | Li et al. | |
| 2024/0408593 A1 | 12/2024 | Kim et al. | |
| 2024/0416315 A1 | 12/2024 | Bava | |
| 2024/0417783 A1 | 12/2024 | Chew et al. | |
| 2024/0417784 A1 | 12/2024 | Sukovich et al. | |
| 2025/0002980 A1 | 1/2025 | Tentori et al. | |
| 2025/0002982 A1 | 1/2025 | Stoeckius et al. | |
| 2025/0003956 A1 | 1/2025 | Delaney et al. | |
| 2025/0019689 A1 | 1/2025 | Galonska et al. | |
| 2025/0019749 A1 | 1/2025 | Katiraee et al. | |
| 2025/0066762 A1 | 2/2025 | Man et al. | |
| 2025/0066770 A1 | 2/2025 | Costa | |
| 2025/0073719 A1 | 3/2025 | Cox et al. | |
| 2025/0075261 A1 | 3/2025 | Kim | |
| 2025/0101501 A1 | 3/2025 | Chee | |
| 2025/0101502 A1 | 3/2025 | Chee | |
| 2025/0101504 A1 | 3/2025 | Nagendran et al. | |
| 2025/0122564 A1 | 4/2025 | Mignardi et al. | |
| 2025/0122565 A1 | 4/2025 | Schnall-Levin et al. | |
| 2025/0129412 A1 | 4/2025 | Uytingco et al. | |
| 2025/0129421 A1 | 4/2025 | Schnall-Levin et al. | |
| 2025/0137043 A1 | 5/2025 | Tentori | |
| 2025/0145984 A1 | 5/2025 | Ma et al. | |
| 2025/0146057 A1 | 5/2025 | Schnall-Levin et al. | |
| 2025/0146058 A1 | 5/2025 | Tentori | |
| 2025/0146071 A1 | 5/2025 | Schnall-Levin et al. | |
| 2025/0146072 A1 | 5/2025 | Schnall-Levin et al. | |
| 2025/0154565 A1 | 5/2025 | Chee | |
| 2025/0154566 A1 | 5/2025 | Chee | |

(56) References Cited

U.S. PATENT DOCUMENTS

| | | |
|---|---|---|
| 2025/0154567 A1 | 5/2025 | Chee |
| 2025/0154568 A1 | 5/2025 | Frisen et al. |
| 2025/0154569 A1 | 5/2025 | Stoeckius et al. |
| 2025/0154571 A1 | 5/2025 | Ramachandran Iyer et al. |
| 2025/0154588 A1 | 5/2025 | Ramachandran Iyer et al. |
| 2025/0155446 A1 | 5/2025 | Uytingco et al. |
| 2025/0163501 A1 | 5/2025 | Singh et al. |
| 2025/0163509 A1 | 5/2025 | Daugharthy et al. |
| 2025/0171833 A1 | 5/2025 | Frisen et al. |
| 2025/0171848 A1 | 5/2025 | Chell et al. |
| 2025/0179475 A1 | 6/2025 | Borgstrom et al. |
| 2025/0182305 A1 | 6/2025 | Tentori et al. |
| 2025/0182503 A1 | 6/2025 | Li et al. |
| 2025/0188526 A1 | 6/2025 | Sukovich et al. |
| 2025/0189483 A1 | 6/2025 | Kim et al. |
| 2025/0197847 A1 | 6/2025 | Kim et al. |
| 2025/0197938 A1 | 6/2025 | Bjorninen |
| 2025/0207125 A1 | 6/2025 | Gupta et al. |
| 2025/0207182 A1 | 6/2025 | Chee |
| 2025/0207183 A1 | 6/2025 | Chee |
| 2025/0207195 A1 | 6/2025 | Chell et al. |
| 2025/0208115 A1 | 6/2025 | Bent |
| 2025/0215482 A1 | 7/2025 | Mignardi et al. |
| 2025/0215484 A1 | 7/2025 | Ramachandran Iyer et al. |
| 2025/0216300 A1 | 7/2025 | Delaney et al. |
| 2025/0216303 A1 | 7/2025 | Cox et al. |
| 2025/0223633 A1 | 7/2025 | Frenz et al. |
| 2025/0230487 A1 | 7/2025 | Chee et al. |
| 2025/0230498 A1 | 7/2025 | Katiraee |
| 2025/0250621 A1 | 8/2025 | Galonska et al. |
| 2025/0250632 A1 | 8/2025 | Mignardi et al. |
| 2025/0257393 A1 | 8/2025 | Katirace et al. |
| 2025/0263791 A1 | 8/2025 | Bava |
| 2025/0264411 A1 | 8/2025 | Bava |
| 2025/0283154 A1 | 9/2025 | Ramachandran Iyer et al. |
| 2025/0283157 A1 | 9/2025 | Uytingco et al. |
| 2025/0297308 A1 | 9/2025 | Tentori |
| 2025/0313890 A1 | 10/2025 | Lundeberg et al. |
| 2025/0313892 A1 | 10/2025 | Stoeckius |
| 2025/0340932 A1 | 11/2025 | Chee |
| 2025/0340933 A1 | 11/2025 | Giacomello et al. |
| 2025/0354931 A1 | 11/2025 | Shah et al. |
| 2025/0369037 A1 | 12/2025 | Gupta |
| 2025/0376676 A1 | 12/2025 | Kim et al. |
| 2025/0376719 A1 | 12/2025 | Shah |
| 2025/0382665 A1 | 12/2025 | Frenz et al. |
| 2026/0002202 A1 | 1/2026 | Schnall-Levin et al. |
| 2026/0009784 A1 | 1/2026 | Stoeckius |
| 2026/0015653 A1 | 1/2026 | Chew et al. |
| 2026/0022419 A1 | 1/2026 | Bent et al. |
| 2026/0035740 A1 | 2/2026 | Chee |
| 2026/0049349 A1 | 2/2026 | Gallant et al. |
| 2026/0055443 A1 | 2/2026 | Tentori et al. |
| 2026/0071262 A1 | 3/2026 | Yin et al. |

FOREIGN PATENT DOCUMENTS

| | | |
|---|---|---|
| EP | 2002017 | 12/2008 |
| EP | 2130913 | 12/2009 |
| EP | 2881465 | 6/2015 |
| EP | 3013984 | 5/2016 |
| EP | 3511423 | 7/2019 |
| EP | 3541956 | 9/2019 |
| JP | 2011-182702 | 9/2011 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 1999/032654 | 7/1999 |
| WO | WO 2000/063437 | 10/2000 |
| WO | WO 2002/059355 | 8/2002 |
| WO | WO 2002/077283 | 10/2002 |
| WO | WO 2002/088396 | 11/2002 |
| WO | WO 2003/002979 | 1/2003 |
| WO | WO 2003/010176 | 2/2003 |
| WO | WO 2004/028955 | 4/2004 |
| WO | WO 2005/007814 | 1/2005 |
| WO | WO 2006/081222 | 8/2006 |
| WO | WO 2007/073171 | 6/2007 |
| WO | WO 2007/076726 | 7/2007 |
| WO | WO 2007/120241 | 10/2007 |
| WO | WO 2007/145612 | 12/2007 |
| WO | WO 2008/075086 | 6/2008 |
| WO | WO 2009/032167 | 3/2009 |
| WO | WO 2009/152928 | 12/2009 |
| WO | WO 2010/088517 | 8/2010 |
| WO | WO 2010/126614 | 11/2010 |
| WO | WO 2011/014879 | 2/2011 |
| WO | WO 2011/068088 | 6/2011 |
| WO | WO 2011/071943 | 6/2011 |
| WO | WO 2012/048341 | 4/2012 |
| WO | WO 2012/061832 | 5/2012 |
| WO | WO 2012/083225 | 6/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/210223 | 12/2014 |
| WO | WO 2015/031691 | 3/2015 |
| WO | WO 2015/188839 | 12/2015 |
| WO | WO-2015200541 A1 * | 12/2015 | ........... C12Q 1/6806 |
| WO | WO 2016/040476 | 3/2016 |
| WO | WO 2016/126871 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2017/019456 | 2/2017 |
| WO | WO 2017/075293 | 5/2017 |
| WO | WO 2017/096158 | 7/2017 |
| WO | WO 2017/124101 | 7/2017 |
| WO | WO 2018/057051 | 3/2018 |
| WO | WO 2018/064640 | 4/2018 |
| WO | WO 2018/075693 | 4/2018 |
| WO | WO 2018/091676 | 5/2018 |
| WO | WO 2018/175779 | 9/2018 |
| WO | WO 2018/217862 | 11/2018 |
| WO | WO 2019/104337 | 5/2019 |
| WO | WO 2019/213254 | 11/2019 |
| WO | WO 2019/213294 | 11/2019 |
| WO | WO 2020/028194 | 2/2020 |
| WO | WO 2020/033164 | 2/2020 |
| WO | WO 2020/041148 | 2/2020 |
| WO | WO 2020/047002 | 3/2020 |
| WO | WO 2020/047010 | 3/2020 |
| WO | WO 2020/076979 | 4/2020 |
| WO | WO 2020/099640 | 5/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |

(56) References Cited

FOREIGN PATENT DOCUMENTS

| WO | WO 2021/133842 | 7/2021 |
|----|----------------|--------|
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/130019 | 7/2023 |
| WO | WO 2023/147355 | 8/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |
| WO | WO 2026/024934 | 1/2026 |

OTHER PUBLICATIONS

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrNOCH17rEkOUXwd19It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrNOCH17rEkOUXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG00023_VisiumSpatialGeneExpression_UserGuide_RevD.pdf>, 70 pages.

Abdelaal et al., "Detection of Antigen-Specific T Cells Using In Situ MHC Tetramer Staining," Int. J. Mol. Sci., Oct. 18, 2019, 20(20):5165, 11 pgs.

Adessi et al., "Solid phase DNA amplification: characterisation of primer attachment and amplification mechanisms," Nucl. Acids Res., 2000, 28(20):E87, 8 pages.

(56) References Cited

OTHER PUBLICATIONS

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Allawi et al., "Thermodynamics and NMR of Internal G.T Mismatches in DNA," Biochemistry, 1996, 36(34):10581-10594.

Angenendt et al., "Cell-free Protein expression and functional assay in a nanowell chip format," Analytical Chemistry, 2004, 76(7):1844-49.

Angenendt et al., "Generation of High Density Protein Microarrays by Cell-free in Situ Expression of Unpurified PCR Products," Molecular and Cellular Proteomics, (2006) Ch. 5.9, pp. 1658-1666.

Armani et al., "2D-PCR: a method of mapping DNA in tissue sections," Lab Chip, 2009, 9(24):3526-34.

Asp et al., "A spatiotemporal organ-wide gene expression and cell atlas of the developing human heart," Cell, Dec. 12, 2019, 179(7):1647-1660.

Asp et al., "Spatially Resolved Transcriptomes—Next Generation Tools for Tissue Exploration," Bioessays, Oct. 2020, 42(10):e1900221, 16 pages.

Atkinson et al., "An Updated Protocol for High Throughput Plant Tissue Sectioning," Front Plant Sci, 2017, 8:1721, 8 pages.

Atkinson, "Overview of Translation: Lecture Manuscript," U of Texas, 2000, DD, pp. 6.1-6.8.

Bains et al., "A novel method for nucleic acid sequence determination," Journal of Theoretical Biology, 1988, 135(3), 303-7.

Baird et al., "Rapid SNP Discovery and Genetic Mapping Using Sequenced RAD markers," PLOS One, 2008, 3(1 0):e3376.

Bakker et al., "Conditional MHC class I ligands and peptide exchange technology for the human MHC gene products HLA-A1, -A3, -A11, and -B7," Proc Natl Acad Sci USA, Mar. 11, 2008, 105(10):3825-3830.

Bang, "DNA synthesis using error-free oligos retrieved from NGS flow-cells," Yonsei University, May 9, 2017, retrieved on Aug. 25, 2021, retrieved from URL <https://diyhpl.us/wiki/transcripts/hgp-write/2017-05-09/microarray-flow-cell-oligos-dna-synthesis/>, 2 pages.

Barnes, "PCR amplification of up to 35-kb DNA with high fidelity and high yield from lambda bacteriophage templates," Proc. Natl. Acad. Sci USA, 1994, 91(6):2216-2220.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

Bentzen et al., "Large-scale detection of antigen-specific T cells using peptide-MHC-I multimers labeled with DNA barcodes," Nat Biotechnol., Oct. 2016, 34(10):1037-1045, 12 pages.

Bergenstråhle et al., "Seamless integration of image and molecular analysis for spatial transcriptomics workflows," BMC Genomics, Jul. 2020, 21(1):482, 7 pages.

Birney et al., "Identification and analysis of functional elements in 1% of the human genome by the Encode pilot project," Nature, 2007, 447(7146):799-816.

Blanchard et al., "High-density oligonucleotide arrays," Biosensors & Bioelectronics, 1996, 11(6-7):687-690.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolotin et al., "MiXCR: software for comprehensive adaptive immunity profiling," Nat Methods., May 2015, 12(5):380-1.

Borm et al., "High throughput human embryo spatial transcriptome mapping by surface transfer of tissue RNA," Abstracts Selected Talks, Single Cell Genomics mtg, (SCG2019), 2019, 1 pages (Abstract Only).

Brandon et al., "Mitochondrial mutations in cancer," Oncogene, 2006, 25(34):4647-4662.

Brenner et al., "Gene expression analysis by massively parallel signature sequencing (MPSS) on microbead arrays," Nat. Biotech., 2000, 18(6):630-634.

Brenner et al., "In vitro cloning of complex mixtures of DNA on microbeads: physical separation of differentially expressed cDNAs," Proc. Natl. Acad. Sci. USA, 2000, 97(4):1665-1670.

Brow, "35—The Cleavase I enzyme for mutation and polymorphism scanning," PCR Applications Protocols for Functional Genomics, 1999, pp. 537-550.

Brown et al., "Retroviral integration: structure of the initial covalent product and its precursor, and a role for the viral IN protein," Proc Natl Acad Sci USA, Apr. 1989, 86(8):2525-9.

Buenrostro et al., "Transposition of native chromatin for multimodal regulatory analysis and personal epigenomics," Nat Methods, Dec. 2013, 10(12):1213-1218.

Bullard et al., "Direct comparison of nick-joining activity of the nucleic acid ligases from bacteriophage T4," Biochem. J. 2006, 398(1):135-144.

Burgess, "A space for transcriptomics," Nature Reviews Genetics, 2016, 17(8):436-7.

Burgess, "Finding structure in gene expression," Nature Reviews Genetics, 2018, 19(5):249, 1 page.

Burgess, "Spatial transcriptomics coming of age," Nat Rev Genet., Jun. 2019, 20(6):317, 1 page.

Burns et al., "Well-less, gel-permeation formats for ultra-HTS," DDT, 2001, 6(12):S40-S47.

Carter et al., "Stabilization of an optical microscope to 0.1 nm in three dimensions," Applied Optics, 2007, 46:421-427.

Cha et al., "Specificity, efficiency, and fidelity of PCR," Genome Res., 1993, 3(3):S18-29.

Chandra et al., "Cell-free synthesis-based protein microarrays and their applications," Proteomics, 2009, 5(6):717-30.

Chatterjee et al., "Mitochondrial DNA mutations in human cancer. Oncogene," 2006, 25(34):4663-4674.

Chatterjee et al., "Protein Microarray On-Demand: A Novel Protein Microarray System," PLos One, 2008, 3(9):e3265, 5 pages.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Chen et al., "Spatial Transcriptomics and In Situ Sequencing to Study Alzheimer's Disease," Cell, Aug. 2020, 182(4):976-991.

Chen et al., "μCB-seq: microfluidic cell barcoding and sequencing for high-resolution imaging and sequencing of single cells," Lab Chip, Nov. 2020, 20(21):3899-3913.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Codeluppi et al., "Spatial organization of the somatosensory cortex revealed by osmFISH," Nature Methods, Nov. 2018, 15:932-935.

Constantine et al., "Use of genechip high-density oligonucleotide arrays for gene expression monitoring," Life Science News, Amersham Life Science, 1998, pp. 11-14.

Credle et al., "Multiplexed analysis of fixed tissue RNA using Ligation in situ Hybridization," Nucleic Acids Research, 2017, 45(14):e128, 9 pages.

Crosetto et al., "Spatially resolved transcriptomics and beyond," Nature Review Genetics, 2015, 16(1):57-66.

Czarnik, "Encoding methods for combinatorial chemistry," Curr Opin Chem Biol., Jun. 1997, 1(1):60-6.

Dahl et al., "Circle-to-circle amplification for precise and sensitive DNA analysis," Proc. Natl. Acad. Sci., 2004, 101(13):4548-4553.

Dahotre et al., "DNA-Barcoded pMHC Tetramers for Detection of Single Antigen-Specific T Cells by Digital PCR," Anal Chem., Feb. 19, 2019, 91(4):2695-2700, 18 pages.

Dalma-Weiszhausz et al., "The affymetrix GeneChip platform: an overview," Methods Enzymol., 2006, 410:3-28.

(56)            References Cited

OTHER PUBLICATIONS

Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
Demaree et al., "Chapter 6: Direct quantification of EGFR variant allele frequency in cell-free DNA using a microfluidic-free digital droplet PCR assay," Methods in Cell Biology, 2019, 148:119-131.
Duncan et al., "Affinity chromatography of a sequence-specific DNA binding protein using Teflon-linked oligonucleotides," Anal. Biochem., 1988, 169(1):104-108.
Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.
Effenberger et al., "FLEXamers: A Double Tag for Universal Generation of Versatile Peptide-MHC Multimers," J Immunol., Apr. 1, 2019, 202(7):2164-2171.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Ertsey et al., "Coverslip Mounted-Immersion Cycled in Situ RT-PCR for the Localization of mRNA in Tissue Sections," Biotechniques, 1998, 24(1):92-100.
Falconnet et al., "Surface engineering approaches to micropattern surfaces for cell-based assays," Biomaterials, Jun. 2006, 27(16):3044-3063.
Fan et al., "Highly parallel SNP genotyping," Cold Spring Symp. Quant. Biol., 68: 69-78, 2003.
Fire et al., "Rolling replication of short DNA circles," Proc. Natl. Acad. Sci., 1995, 92(10):4641-4645.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency (Supplemental Materials)," bioRxiv, 2021, 12 pages.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "High density peptide microarrays. In situ synthesis and applications," Molecular Diversity, 8, 177-187, 2004.
Gao et al., "Q&A: Expansion microscopy," BMC Biology, 15:50, 9 pages, 2017.
Gee et al., "Antigen Identification for Orphan T Cell Receptors Expressed on Tumor-Infiltrating Lymphocytes," Cell, Jan. 25, 2018, 172(3):549-563.

Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "High-throughput single-cell activity-based screening and sequencing of antibodies using droplet microfluidics," Nature Biotechnology, Jun. 2020, 38(6):715-721, 19 pages.
Gerdtsson et al., "Evaluation of Solid Supports for Slide- and Well-Based Recombinant Antibody Microarrays", Microarrays (2016) 5:16, 2016.
Giam et al., "Scanning probe-enabled nanocombinatorics define the relationship between fibronectin feature size and stem cell fate," PNAS, Mar. 2012, 109(12):4377-4382.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Gohil, "Evaluation of enzymatically crosslinked ijectable glycol chitosan hydrogel," Journal of Materials Chemistry B, 2015, 3:5511-5522.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, Cell Genomics, posted Jul. 25, 2020, published Dec. 8, 2021, 1(3):100065, 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hatori et al., "Particle-Templated Emulsification for Microfluidics-Free Digital Biology," Anal. Chem., 2018, 90:9813-9820.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Hejatko et al., "In situ hybridization technique for mRNA detection in whole mount Arabidopsis samples," Nature Protocols, 2006, 1(4):1939-1946.
Hiatt et al., "Parallel, tag-directed assembly of locally derived short sequence reads," Nature Methods, 2010, 7(2):119-25.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA, 2008, 105:1176-1181.
Kozlov et al., "A High-Complexity Multiplexed Solution-Phase Assay for Profiling Protease Activity on Microarrays," Comb. Chem. And High Throughput, 11: 24-35, 2008.
Kozlov et al., "A highly scalable peptide-based assay system for proteomics," PLoS ONE, 2012, 7(6):e37441, 10 pages.

(56)  References Cited

OTHER PUBLICATIONS

Kristensen et al., "High-Throughput Methods for Detection of Genetic Variation," BioTechniques, Feb. 2001, 30(2):318-332.
Kuhn et al., "A novel, high-performance random array platform for quantitative gene expression profiling," Genome Res, 2004, 14:2347-2356.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Lee et al., "Protein nanoarrays generated by dip-pen nanolithography," Science, Mar. 2002, 295(5560):1702-1705.
Leriche et al., "Cleavable linkers in chemical biology," Bioorganic & Medicinal Chemistry, 2012, 20:571-582.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Liu et al., "Surface and interface control on photochemically initiated immobilization," J Am Chem Soc., Nov. 2006, 128(43):14067-72.
Lizardi et al., "Mutation detection and single-molecule counting using isothermal rolling-circle amplification," Nat. Genet., 1998, 19(3):225-232.
Lundberg et al., "Multiplexed homogeneous proximity ligation assays for high-throughput protein biomarker research in serological material," Mol Cell Proteomics, 2011, 10(4):M110.004978, 11 pages.
MacBeath et al., "Printing proteins as microarrays for high-throughput function determination," Science, Sep. 2000, 289(5485):1760-1763.
Macosko et al., "Highly Parallel Genome-wide Expression Profiling of Individual Cells Using Nanoliter Droplets," Cell, 2015, 161:1202-1214.
Marsden et al., "3D small-molecule microarrays," Chem. Commun., 2009, pp. 7107-7109.
Marx, "Method of the Year: spatially resolved transcriptomics," Nature Methods, 2021, 18(1):9-14.
Mcgee, "Structure and Analysis of Affymetrix Arrays," UTSW Microarray Analysis Course, Oct. 28, 2005, 68 pages.
McShan et al., "Peptide exchange on MHC-I by TAPBPR is driven by a negative allostery release cycle," Nat Chem Biol., Aug. 2018, 14(8):811-820, 26 pages (Author Manuscript).
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.

Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Nakamura et al., "Biocompatible inkjet printing technique for designed seeding of individual living cells," Tissue Eng, Nov. 2005, 11(11-12):1658-1666.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak, "Entering the Postgenome Era," Science, 1995, 270(5235):368-71.
Ostuni et al., "Patterning Mammalian Cells Using Elastomeric Membranes," Langmuir, Aug. 2000, 16(20):7811-7819.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gene," Proc Natl Acad Sci USA, Jun. 1992, 89(12):5577-5581.
Petterson et al., "Generations of sequencing technologies," Genomics, 2009, 93(2):105-111.
Polsky-Cynkin et al., "Use of DNA immobilized on plastic and agarose supports to detect DNA by sandwich hybridization," Clin. Chem., 1985, 31(9):1438-1443.
Rajan et al., "Recombinant Human B Cell Repertoires Enable Screening for Rare, Specific, and Natively Paired Antibodies," Commun Biol., Jan. 22, 2018, 1:5, pp. 1-8.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rush et al., "New Aldehyde Tag Sequences Identified by Screening Formylglycine Generating Enzymes in Vitro and in Vivo," J. of American Chemical Society, Aug. 2008, 130(37): 12240-12241.
Sack et al., "Express photolithographic DNA microarray synthesis with optimized chemistry and high-efficiency photolabile groups," Journal of Nanobiotechnology, Mar. 2016, 14:14, 13 pages.
Sakai et al., "Cell-selective encapsulation in hydrogel sheaths via biospecific identification and biochemical cross-linking," Biomaterials, 2015, 53:494-501.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schaus et al., "A DNA nanoscope via auto-cycling proximity recording," Nat. Commun., 2017, 8:696, 10 pages.
Schena et al., "Quantitative monitoring of gene expression patterns with a complementary DNA microarray," Science, Oct. 1995, 270(5235):467-470.

(56) References Cited

OTHER PUBLICATIONS

Schlapak et al., "Glass surfaces grafted with high-density poly (ethylene glycol) as substrates for DNA oligonucleotide microarrays," Langinuir, Jan. 2006, 22: 277-285.

Segaliny et al., "Functional TCR T cell screening using single-cell droplet microfluidics†," Lab Chip, 2018, 3733-3749.

Setliff et al., High-Throughput Mapping of B Cell Receptor Sequences to Antigen Specificity, Cell, 2019, 179:1636-1646.

Seurynck-Servoss et al., "Evaluation of Surface Chemistries for Antibody Microarrays," Anal Biochem., 371(1):105-115, 2007.

Shalon et al., "A DNA microarray system for analyzing complex DNA samples using two-color fluorescent probe hybridization," Genome Res., Jul. 1996, 6(7):639-45.

Shendure et al., "Accurate multiplex polony sequencing of an evolved bacterial genome," Science, 2005, 309(5741):1728-1732.

Shiakolas et al., "Efficient discovery of SARS-CoV-2-neutralizing antibodies via B cell receptor sequencing and ligand blocking," Nature Biotechnology, Aug. 2022, 40:1270-1275.

Sokal et al., "Maturation and persistence of the anti-SARS-CoV-2 memory B cell response," Cell, Mar. 4, 2021, 184(5):1201-1213.

Spurgeon et al., "High Throughput Gene Expression Measurement with Real Time PCR in a Microfluidic Dynamic Array," Plos ONE, 2008, 3(2):e1662.

Stahl et al., "Visualization and analysis of gene expression in tissue sections by spatial transcriptomics," Science, Jul. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides," Proc Natl Acad Sci USA, Jul. 1995, 92(14):6379-83.

Strell et al., "Placing RNA in context and space—methods for spatially resolved transcriptomics," The FEBS Journal, 2019, 286(8):1468-1481.

Suh et al., "A simple soft lithographic route to fabrication of poly(ethylene glycol) microstructures for protein and cell patterning," Biomaterials, Feb. 2004, 25(3):557-563.

Sun et al., "Direct immobilization of DNA probes on non-modified plastics by UV irradiation and integration in microfluidic devices for rapid bioassay," Anal. Bio. Chem., 402: 741-748, 2012.

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

Takei et al., "Integrated Spatial Genomics Reveals Global Architecture of Single Nuclei," Nature, Jan. 27, 2021, 590(7845):344-350, 53 pages.

Tan et al., "Parylene peel-off arrays to probe the role of cell-cell interactions in tumour angiogenesis," Integr Biol (Camb), Oct. 2009, 1(10):587-594.

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.

Twyman et al., "Techniques Patents for SNP Genotyping," Pharmacogenomics, Jan. 2003, 4(1):67-79.

Valkiers et al., "Recent advances in T-cell receptor repertoire analysis: Bridging the gap with multimodal single-cell RNA sequencing," ImmunoInformatics, 2022, 5:100009, 17 pages.

Van Gelder et al., "Amplified RNA synthesized from limited quantities of heterogeneous cDNA," Proc. Natl. Acad. Sci. USA, 1990, 87(5):1663-1667.

Vasiliskov et al., "Fabrication of microarray of gel-immobilized compounds on a chip by copolymerization," Biotechniques, Sep. 1999, 27(3):592-606.

Vickovic et al., "High-definition spatial transcriptomics for in situ tissue profiling," Nat Methods, Oct. 2019, 16(10):987-990.

Vickovic et al., "SM-Omics: An automated Platform for High-Throughput Spatial Multi-Omics," bioRxiv, Oct. 2020, 40 pages.

Vlassakis et al., "Effect of Polymer Hydration State on In-Gel Immunoassays," Anal Chem., Nov. 2015, 87(21):11030-8.

Vogelstein et al., "Digital PCR," Proceedings of the National Academy of Sciences, Aug. 1999, 96(16):9236-9241.

Walker et al., "Strand displacement amplification—an isothermal, in vitro DNA amplification technique," Nucleic Acids Research, 1992, 20(7):1691-1696.

Wang et al., "High-fidelity mRNA amplification for gene profiling," Nature Biotechnology, Apr. 2000, 18(4):457-459.

Wang et al., "Imaging-based pooled CRISPR screening reveals regulators of lncRNA localization," Proc Natl Acad Sci USA, May 2019, 116(22):10842-10851.

Worthington et al., "Cloning of random oligonucleotides to create single-insert plasmid libraries," Anal Biochem, 2001, 294(2):169-175.

Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.

Yershov et al., "DNA analysis and diagnostics on oligonucleotide microchips," Proc. Natl. Acad. Sci. USA, May 1996, 93(10):4913-4918.

Zhang et al., "High-throughput determination of the antigen specificities of T cell receptors in single cells," Nat Biotechnol., Nov. 12, 2018, 12 pages (Author Manuscript).

Zhu et al., "Reverse transcriptase template switching: a SMART approach for full-length cDNA library construction," Biotechniques, Apr. 2001, 30(4):892-897.

10x Genomics, "Assay Scheme and Configuration of Chromium™ Single Cell V(D)J Libraries," 10x Genomics, CG000109 Rev D, 2017, 10 pages.

Chou et al., "Optimization of probe length and the number of probes per gene for optimal microarray analysis of gene expression," Nucleic acids research, 2004, 32(12):e99, 8 pages.

Hong et al., "Cell Microarray Technologies for High-Throughput Cell-Based Biosensors," Sensors (Basel), Jun. 5, 2017, 17(6):1293.

Stickels et al., "Highly sensitive spatial transcriptomics at near-cellular resolution with Slide-seqV2," Nat Biotechnol., Mar. 2021, 39(3):313-319, 28 pages (Author Manuscript).

* cited by examiner

1 Generate linear polyacrylamide chains acrylamide sodium formate

Figure 2:
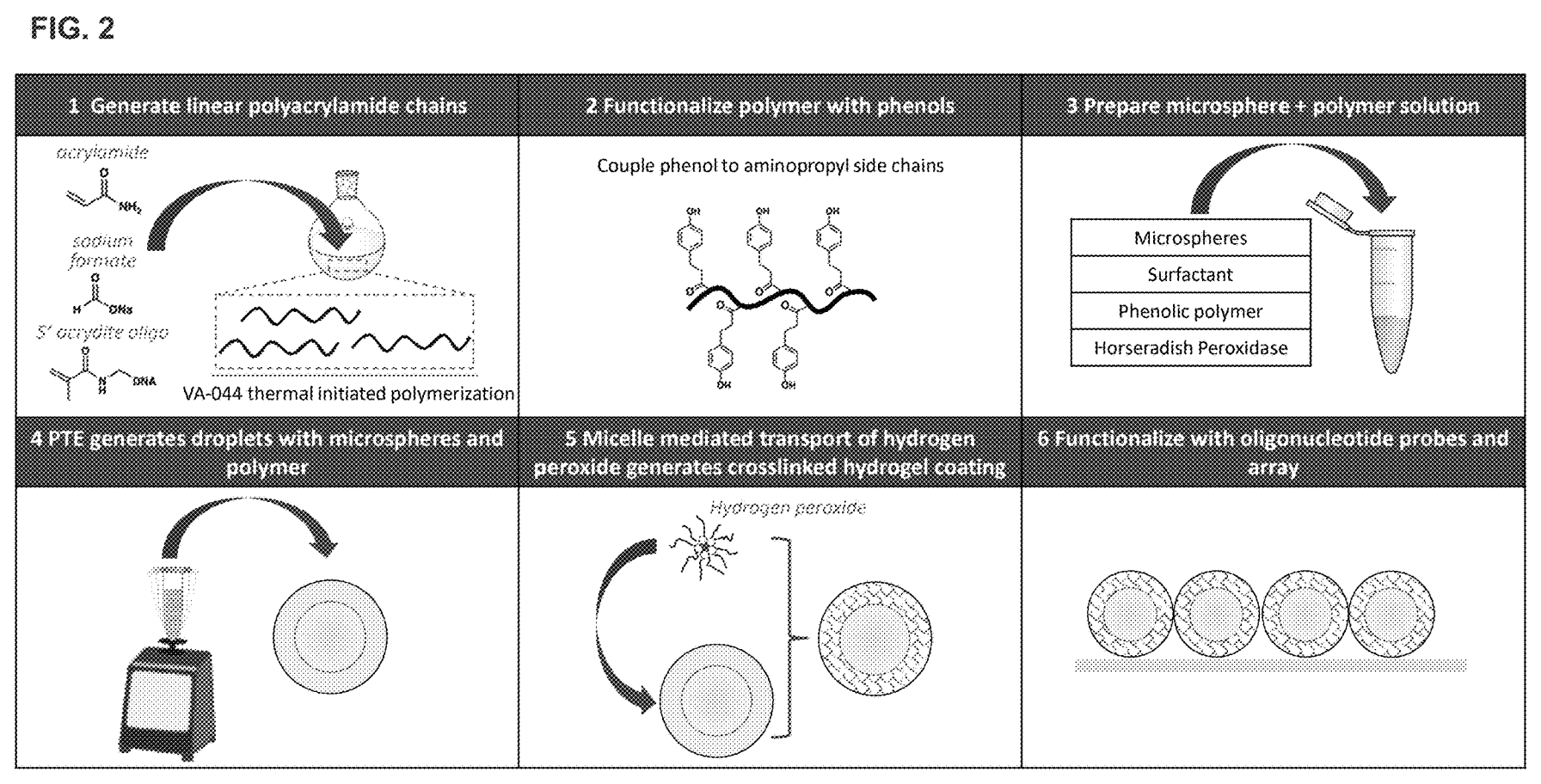

5' acrydite oligo

VA-044 thermal initiated polymerization

2 Functionalize polymer with phenols

Couple phenol to aminopropyl side chains

3 Prepare microsphere + polymer solution

| Microspheres |
| Surfactant |
| Phenolic polymer |
| Horseradish Peroxidase |

4 PTE generates droplets with microspheres and polymer

5 Micelle mediated transport of hydrogen peroxide generates crosslinked hydrogel coating

Hydrogen peroxide

6 Functionalize with oligonucleotide probes and array

METHODS AND COMPOSITIONS RELATED TO MICROSPHERE SURFACE GELATION

CROSS-REFERENCE TO RELATED APPLICATION

This application claims the benefit of U.S. Provisional Patent Application 63/323,049, filed Mar. 23, 2022, which is incorporated herein by reference in entirety and for all purposes.

FIELD

The present disclosure relates generally to the field of spatial transcriptomics and particularly to compositions and methods useful for the spatially resolved analysis of transcripts from biological samples. More particularly, the present disclosure relates to compositions and methods for generating hydrogel coatings on features useful for the capture of cellular transcripts.

BACKGROUND

Biological tissues are composed of diverse cells, extracellular matrix, and complex signaling systems organized to interact and execute complex functions. It has been well established that tissue functions essentially rely on the precise spatial organization of cells characterized by distinct molecular profiles. In particular, cells within a tissue have differences in cell morphology and/or function due to varied levels of biomolecules and metabolites within the different cells. Therefore, determining the spatial distribution of biomolecules can be of great significance for life sciences research, molecular diagnostics and many other applications. In addition to understanding the gene expression profile of a particular cell or tissue, spatial information of biomolecules (e.g., nucleic acids, chemical metabolites, proteins) within the cell or tissue may also provide valuable information. For example, gene expression profiling of cancer cells can be important for monitoring cancer therapy.

Spatial transcriptomics platforms, in general, involve the transfer and capture of cellular transcripts from a thin tissue section to barcoded oligonucleotide probes. The capture probes are generally immobilized on features, and while the features may take a variety of forms, one potential candidate is a solid, spherical bead called a microsphere.

Microspheres offer the advantage of highly uniform size distribution, and they are commercially available in a range of sizes (e.g., micrometer scale) and materials. However, there is concern that the solid microsphere surface has limited oligonucleotide capture probe loading capacity and the capture probe concentration may be too low to support cellular assays at the desired sensitivity. Additionally for spatial transcriptomic assays, solid microspheres may possess optical properties that interfere with staining and/or imaging such that the solid microspheres may obstruct or obscure histological features or spatial biomolecule data.

Therefore, there remains a need in the art for compositions and methods for increasing the oligonucleotide loading capacity of microspheres and for improving optical properties of solid microspheres, thereby enhancing the sensitivity of spatial transcriptomic platforms.

SUMMARY

The present disclosure relates generally to compositions including hydrogel-coated features, methods of preparing hydrogel-coated features, methods for spatial analysis employing the hydrogel-coated features, and kits including the hydrogel-coated features. In particular, as described in greater detail below, some embodiments of the disclosure provide a hydrogel-coated feature including a solid particle and a hydrogel encapsulating the solid particle, wherein the hydrogel comprises a crosslinked polymer and a plurality of moieties.

In some embodiments, each moiety of the plurality of moieties comprises an oligonucleotide, wherein the oligonucleotide is configured to hybridize to a capture probe. In some embodiments, each moiety of the plurality of moieties comprises an organic functional group, wherein the organic functional group is capable of attachment to a capture probe. In some embodiments, the organic functional group is an amine group.

In some embodiments, the hydrogel includes an acrylamide copolymer. In some embodiments the acrylamide copolymer is prepared from acrylamide and 3-aminopropyl methacrylamide monomers. In some embodiments, the acrylamide copolymer is prepared from acrylamide, 3-aminopropyl methacrylamide, and 5' acrydite oligonucleotide monomers. In some embodiments, the acrylamide copolymer is prepared in the presence of sodium formate. In some embodiments, the acrylamide copolymer is prepared in the presence of a polymerization initiator. In some embodiments, the polymerization initiator is a water-soluble azo polymerization initiator, preferably VA-044.

In some embodiments, the organic functional group is phenol. In some embodiments, the phenol is attached to a linear chain of the acrylamide polymer via an amide coupling reaction.

In an aspect of the disclosure, provided herein are hydrogel coated features where the hydrogel includes a cleavable functionality and wherein the hydrogel can be degraded by cleavage of the cleavable functionality. In some embodiments, the crosslinks between linear chains of the acrylamide polymer in the hydrogel comprise the cleavable functionality.

In some embodiments, the solid particles of the disclosure are microspheres, optionally wherein the microspheres have a diameter of about 1 micrometer to about 100 micrometers. In some embodiments, the microspheres include polystyrene, carboxyl-modified polystyrene, polystyrene/2% divinylbenzene, polystyrene/10% divinylbenzene, polystyrene/55% divinylbenzene, polymethyl methacrylate or silica.

In some embodiments, the hydrogel-coated features of the disclosure include a plurality of capture probes, wherein each capture probe is attached to a moiety of the plurality of moieties within the hydrogel.

In some embodiments, the capture probe includes a barcode sequence and a capture domain. In some embodiments, the capture domain includes a poly(T) sequence, a random sequence, a gene specific sequence, or a degenerate sequence.

In some embodiments, the capture probe further includes a unique molecular identifier (UMI) and/or a functional domain.

In some embodiments, the feature includes a plurality of capture probes at an average density of about 1,000 to about 100,000 capture probes per micrometer$^2$. In some embodiments, the average density is about 10,000 to about 80,000 capture probes per micrometer$^2$. In some embodiments, the average density is about 25,000 to about 60,000 capture probes per micrometer$^2$.

In one aspect, provided herein is a substrate including a plurality of the hydrogel-coated features of the disclosure, wherein the hydrogel-coated features are immobilized on the substrate. In some embodiments, the hydrogel-coated features are spatially ordered in an array and wherein each the hydrogel-coated feature of the plurality of the hydrogel-coated features is associated with a unique spatial location on the array. In some embodiments, the substrate includes glass, silicon dioxide or a silicon wafer.

In another aspect, the disclosure provides methods of preparing a hydrogel-coated feature, wherein the methods include: (a) providing a solid particle; and (b) encapsulating the solid particle with a hydrogel comprising a crosslinked polymer and a plurality of moieties. In some embodiments, step (b) of such methods include mixing the solid particle, a plurality of linear chains of a polymer, an enzyme, and a substrate for the enzyme, wherein the mixing is performed under conditions in which the enzyme mediates crosslinking of the linear chains to produce a crosslinked polymer, thereby producing a hydrogel that encapsulates the solid particle.

In some embodiments, the enzyme is attached to the solid particle. In some embodiments, the enzyme is attached to the solid particle via an antibody.

In some embodiments of the methods of preparing a hydrogel-coated feature, step (b) includes: (i) mixing an aqueous suspension having the solid particle, a plurality of linear polymer chains of the polymer wherein each linear polymer chain includes a functional group, an enzyme whose enzymatic activity induces crosslinking of the functional group, and a surfactant with a partitioning oil, thereby creating an emulsion in which the solid particle, a plurality of the linear polymer chains, and the enzyme are partitioned into a droplet, and (ii) adding a substrate for the enzyme, under conditions in which the enzyme activity mediates crosslinking of the linear polymer chains to produce the crosslinked polymer, thereby producing a hydrogel that encapsulates the solid particle.

In some embodiments, the methods include repeating steps (i)-(ii) one or more times to encapsulate the solid particle with one or more additional layer(s) of hydrogel. In some embodiments, each of the one or more additional layer(s) comprises a thickness of about 1 micrometer to about 20 micrometers, optionally wherein the total thickness of the hydrogel encapsulating the solid particle is in the range of about 1 micrometer to about 100 micrometers.

In some embodiments of the methods of the disclosure, the enzyme is a peroxidase, a transglutaminase, a tyrosinase, a laccase, a phosphatase, an oxidoreductase, or a metalloproteinase. In some embodiments, the enzyme is a peroxidase and/or the functional group is phenol, acetylacetone, or dihydrotetrazine. In some embodiments, the peroxidase is horseradish peroxidase, optionally wherein the substrate for the enzyme is hydrogen peroxide.

In some embodiments of the methods of preparing a hydrogel-coated feature, each moiety of the plurality of moieties includes an oligonucleotide that is capable of hybridizing to a capture probe. In some embodiments, each moiety of the plurality of moieties includes an organic functional group, wherein the organic functional group is capable of attachment to a capture probe. In some embodiments, the organic functional group is an amine group.

In some embodiments, the hydrogel-coated solid particle includes a plurality of capture probes wherein each capture probe of the plurality of capture probes is attached to a moiety of the plurality of moieties within the hydrogel.

In some embodiments of the methods of the disclosure, the capture probe includes a barcode sequence and optionally a capture domain. In some embodiments, the capture domain includes a poly(T) sequence, a random sequence, a gene specific sequence, or a degenerate sequence. In some embodiments, the capture probe further includes a unique molecular identifier (UMI) and/or a functional domain.

In some embodiments of the methods of the disclosure the hydrogel includes an acrylamide copolymer. In some embodiments, the acrylamide copolymer is prepared from acrylamide and 3-aminopropyl methacrylamide monomers. In some embodiments, the acrylamide copolymer is prepared from acrylamide, 3-aminopropyl methacrylamide, and 5' acrydite oligonucleotide monomers. In some embodiments of the methods of the disclosure, the acrylamide copolymer is prepared in the presence of sodium formate.

In some embodiments of the disclosure, each chain in the plurality of linear polymer chains conforms to the formula $(C_3H_5NO)_n$, wherein n is in the range of about 5-1000.

In some embodiments of the methods of the disclosure, the functional group is phenol. In some embodiments, the phenol is attached to the linear chain of the polymer via an amide coupling reaction.

In some embodiments of the methods of the disclosure, the hydrogel includes a cleavable functionality, wherein the hydrogel can be degraded by cleavage of the cleavable functionality. In some embodiments, the crosslinks between linear chains of the polymer in the hydrogel comprise the cleavable functionality.

In another aspect, the disclosure provides hydrogel-coated features produced by the methods of the disclosure, and compositions thereof. In some embodiments, the hydrogel-coated features include a plurality of capture probes affixed thereon. In some embodiments, the feature includes a plurality of capture probes at an average density of about 1000-100,000 capture probes per micrometer$^2$, preferably, 10,000-80,000 capture probes per micrometer$^2$, more preferably, 25,000-60,000 capture probes per micrometer$^2$.

In yet another aspect, the disclosure provides substrates including the hydrogel-coated features produced by the methods of the disclosure. In some embodiments, the hydrogel-coated features include a plurality of capture probes affixed thereon, wherein each capture probe includes a barcode sequence. In some embodiments, the capture probes of each hydrogel-coated feature are different from the barcode sequence on the capture probes of any other hydrogel-coated feature on the substrate.

In another aspect, the disclosure provides herein, methods for preparing a plurality of hydrogel-coated features, the methods include: (a) suspending a plurality of features in an aqueous solution having a linear polymer, a surfactant, and an enzyme, thereby forming a suspension comprising the plurality of features, (b) adding an oil to the suspension and emulsifying the suspension into a plurality of droplets, wherein a droplet of the plurality of droplets include a feature of the plurality of features coated with the linear polymer and the enzyme, (c) contacting the plurality of droplets with a substrate for the enzyme, wherein the enzyme activity mediates crosslinking of the linear polymer to form a hydrogel on a feature of the plurality of features, thereby forming a plurality of hydrogel-coated features.

In some embodiments of the methods of the disclosure, the linear polymer comprises a plurality of linear chains wherein each linear chain comprises a functional group. In some embodiments, the functional group is phenol, acetylacetone or dihydrotetrazine group. In some embodiments, the linear polymer is a phenolic linear polyacrylamide polymer.

In some embodiments, the methods for preparing a plurality of hydrogel-coated features further include the step of preparing the phenolic linear polyacrylamide polymer by (i) combining acrylamide, sodium formate, and 5'-acrydite modified oligonucleotides in aqueous solution with a polymerization initiator under conditions suitable for polymerization of the acrylamide, thereby forming linear polyacrylamide chains; and (ii) functionalizing the linear polyacrylamide chains with phenol.

In some embodiments, step (i) includes combining acrylamide, sodium formate, 5'-acrydite modified oligonucleotides and N-(3-aminopropyl) methacrylamide HCL with the polymerization initiator. In some embodiments, functionalizing the linear polyacrylamide chains with phenol includes coupling phenol to aminopropyl side chains.

In some embodiments of the methods of preparing hydrogel-coated features, the linear polyacrylamide chains are further functionalized with acetylacetone or dihydrotetrazine.

In some embodiments of the methods provided herein, the polymerization initiator is a water-soluble azo polymerization initiator, preferably VA-044. In some embodiments, the surfactant is Triton X-100 or Tween-20.

In some embodiments of the methods herein, the oil is a fluorinated oil, a silicone oil, or a hydrocarbon oil.

In some embodiments of the methods provided herein, the step of emulsifying the suspension includes agitation, preferably vortexing.

Non-limiting examples of the enzymes used with the methods of preparing hydrogel-coated features of the disclosure, include peroxidases, transglutaminases, tyrosinases, laccases, phosphatases, oxidoreductases, or metalloproteinases. In some embodiments, the peroxidase is horseradish peroxidase. In some embodiments, the substrate for the enzyme is hydrogen peroxide.

In some embodiments of the methods provided herein, methods include repeating steps (a)-(c) one or more times to encapsulate a hydrogel-coated feature in the plurality of hydrogel-coated features with one or more additional layer(s) of hydrogel. In some embodiments, each of the one or more additional layer(s) has a thickness of about 1 micrometer to about 20 micrometers, optionally wherein the total thickness of the hydrogel encapsulating the hydrogel-coated feature is in the range of about 1 micrometer to about 100 micrometers.

In some embodiments of the methods of the disclosure, the features are microspheres. In some embodiments, the microspheres have a diameter of about 0.1 μm to about 5 μm, about 1 μm to about 10 μm, about 1 μm to about 20 μm, about 1 μm to about 30 μm, about 1 μm to about 40 μm, about 1 μm to about 50 μm, about 1 μm to about 60 μm, about 1 μm to about 70 μm, about 1 μm to about 80 μm, about 1 μm to about 90 μm, about 90 μm to about 100 μm, about 80 μm to about 100 μm, about 70 μm to about 100 μm, about 60 μm to about 100 μm, about 50 μm to about 100 μm, about 40 μm to about 100 μm, about 30 μm to about 100 μm, about 20 μm to about 100 μm, or about 10 μm to about 100 μm.

In some embodiments of the methods of the disclosure, the microsphere is a polystyrene, carboxyl-modified polystyrene, polystyrene/2% divinylbenzene, polystyrene/10% divinylbenzene, polystyrene/55% divinylbenzene, or polymethyl methacrylate microsphere. In some embodiments, the microsphere is modified by one or more of silane deposition and polymer adsorption.

In some embodiments of the methods of preparing hydrogel-coated features, the methods further comprise the step of attaching a capture probe to a moiety within the hydrogel. In some embodiments, the capture probe includes a barcode and a capture domain, wherein the capture domain is capable of binding to an analyte, and wherein the barcode is different for each hydrogel-coated feature of the plurality of hydrogel-coated features. In some embodiments, the capture probe further includes a unique molecular identifier (UMI) and/or a functional domain. In some embodiments, the capture domain includes a poly(T) sequence, a random sequence, a gene specific sequence or a degenerate sequence.

In some embodiments of the methods of the disclosure, the hydrogel-coated features include a plurality of capture probes at an average density of about 1000-100,000 capture probes per micrometer$^2$, preferably, 10,000-80,000 capture probes per micrometer$^2$, more preferably, 25,000-60,000 capture probes per micrometer$^2$.

In some embodiments of the methods of the disclosure, the moiety of the hydrogel includes an oligonucleotide and wherein attaching the capture probe to the hydrogel includes hybridizing the capture probe to the oligonucleotide. In some embodiments, the moiety includes an organic functional group, and wherein attaching the capture probe to the hydrogel includes attaching the capture probe to the organic functional group. In some embodiments, the organic functional group is an amine group.

In some embodiments of the methods provided herein, when the capture domain of the capture probe is capable of binding to an analyte, the analyte is RNA (e.g., mRNA) or DNA (e.g., genomic DNA, RNA Templated Ligation (RTL) probes).

In some embodiments, the methods provided herein further include a step of attaching a plurality of hydrogel-coated features to a substrate. In some embodiments, the plurality of the hydrogel-coated features is attached to the substrate in a spatially ordered array, wherein each hydrogel-coated feature of the plurality of hydrogel-coated features occupies a distinct spatial location on the substrate, and wherein the methods further include associating each hydrogel-coated feature of the plurality of hydrogel-coated features with its spatial location on the substrate. In some embodiments, the associating step includes determining the sequence of a spatial barcode of a hydrogel-coated feature of the plurality of hydrogel-coated features and associating the determined spatial barcode sequence with the location of the hydrogel-coated feature on the substrate.

In some embodiments, the determining step includes sequencing. In some embodiments, the sequencing is in situ sequencing. In some embodiments, the in situ sequencing is performed via sequencing-by-synthesis (SBS), sequential fluorescence hybridization, sequencing by ligation, nucleic acid hybridization, or high-throughput digital sequencing techniques.

In another aspect of the disclosure, provided herein are a plurality of hydrogel-coated features prepared by the methods of the disclosure.

In yet another aspect, the disclosure provides substrates including a plurality of hydrogel-coated features attached thereto, wherein the plurality of hydrogel-coated features is prepared by the methods of the disclosure.

In another aspect, provided herein are methods of immobilizing a capture probe on a feature, the methods including: (a) encapsulating a solid particle with a hydrogel including a crosslinked polymer, and (b) attaching the capture probe to a moiety within the hydrogel. In some embodiments, the moiety includes an oligonucleotide, and wherein step (b) includes hybridizing the capture probe to the oligonucleotide. In some embodiments, the moiety includes an organic functional group, and wherein step (b) includes attaching the capture probe to the organic functional group. In some embodiments step (a) includes: mixing the solid particle, a plurality of linear chains of the polymer wherein each linear chain includes s a functional group, an enzyme, and a substrate for the enzyme, wherein the mixing is performed under conditions in which the enzyme activity mediates crosslinking of the linear chains to produce a crosslinked polymer, thereby producing a hydrogel that encapsulates the solid particle.

In some embodiments of the methods of immobilizing capture probes on a feature, the enzyme is attached to the feature. In some embodiments, step (a) includes: (i) mixing an aqueous suspension including the solid particle, a plurality of linear chains of the polymer wherein each linear chain comprises a functional group, an enzyme whose enzymatic activity is capable of inducing crosslinking of the functional group, and a surfactant with a partitioning oil, thereby creating an emulsion in which the solid particle, a plurality of the linear polymer chains, and the enzyme are partitioned into a droplet; and (ii) adding a substrate for the enzyme, under conditions in which the enzyme mediates crosslinking of the linear polymer chains to produce the crosslinked polymer, thereby producing a hydrogel that encapsulates the solid particle.

In some embodiments of the methods for immobilizing a capture probe on a hydrogel-coated feature, the method includes repeating steps (i)-(ii) one or more times to encapsulate the solid particle with one or more additional layer(s) of hydrogel.

In another aspect, the disclosure provides methods for preparing a plurality of hydrogel-coated features, the methods include: (a) suspending a plurality of features in an aqueous solution comprising a polymerizable monomer and a surfactant, thereby forming a suspension of features; (b) adding a partitioning oil to the suspension and emulsifying the suspension into a plurality of droplets, wherein a droplet of the plurality of droplets includes a feature of the plurality of features coated with the monomer; (c) contacting the plurality of droplets with a polymerization agent such that the monomer coating a feature of the plurality of features is polymerized to form a plurality of hydrogel-coated features.

In another aspect, the disclosure provides methods for spatial analysis of a biological analyte in a biological sample, the method includes: (a) providing a substrate including the hydrogel-coated features of the disclosure; (b) contacting the substrate with a biological sample under conditions sufficient for at least one biological analyte of the biological sample, or a proxy or intermediate thereof, to hybridize to a capture probe on at least one hydrogel-coated feature; and (c) determining (i) all or a part of the sequence of the biological analyte, or the proxy or intermediate thereof, hybridized to the capture probe, or a complement thereof, and (ii) the spatial barcode, or a complement thereof, and using the determined sequence of (i) and (ii) to identify the location of the biological analyte in the biological sample. In some embodiments, the spatial resolution for the location of the biological analyte in the biological sample is increased as compared to a reference spatial resolution achieved using a corresponding method where the method comprises a feature that does not comprise a hydrogel. In some embodiments, the biological sample comprises fresh tissue, frozen tissue, or fixed tissue, such as formalin fixed, or formalin-fixed, paraffin-embedded tissue.

In some embodiments of the methods for spatial analysis of a biological analyte in a biological sample, the methods further include contacting the biological sample to the substrate and/or permeabilizing the biological sample to release the biological analyte therefrom, optionally wherein the permeabilizing includes the use of an organic solvent, a detergent, an enzyme, or a combination thereof. In some embodiments, the biological analyte is a nucleic acid. In some embodiments, the nucleic acid is mRNA, gDNA, RNA, or tRNA. In some embodiments, the biological analyte is a protein.

In some embodiments, the method further includes fixing the biological sample. In some embodiments, fixing the biological sample includes the use of a fixative such as ethanol, methanol, acetone, formaldehyde, paraformaldehyde-Triton, glutaraldehyde, and combinations thereof. In some embodiments, the methods further include staining the biological sample. In some embodiments, the staining includes use of eosin and/or hematoxylin. In some embodiments, the staining includes the use of a detectable label such as a radioisotope, a fluorophore, a chemiluminescent compound, a bioluminescent compound, or a combination thereof. In some embodiments, the methods further include imaging the biological sample.

In some embodiments of the methods of spatial analysis, the determining in step (c) includes sequencing. In some embodiments, the sequencing includes high-throughput sequencing.

In another aspect, the disclosure provides kits with instructions for use thereof, one or more substrates comprising hydrogel-coated features of the disclosure, wherein the kit is for the spatial analysis of a biological analyte in a biological sample. In some embodiments, the biological analyte is a nucleic acid such as mRNA, gDNA, RNA, or tRNA. In some embodiments, the biological analyte is a protein. In some embodiments, the kit further includes fixatives for fixing the biological sample. In some embodiments, the kit includes a fixative such as ethanol, methanol, acetone, formaldehyde, paraformaldehyde-Triton, glutaraldehyde, or combinations thereof for fixing the biological sample. In some embodiments, the kit further includes staining reagents for staining the biological sample. In some embodiments, the staining reagent is eosin and/or hematoxylin. In some embodiments, the kit includes a detectable label such as a radioisotope, a fluorophore, a chemiluminescent compound, a bioluminescent compound, or a combination thereof for use in staining the biological sample.

Each of the aspects and embodiments described herein may be capable of being used together, unless excluded either explicitly or clearly from the context of the embodiment or aspect.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

Figure 1:
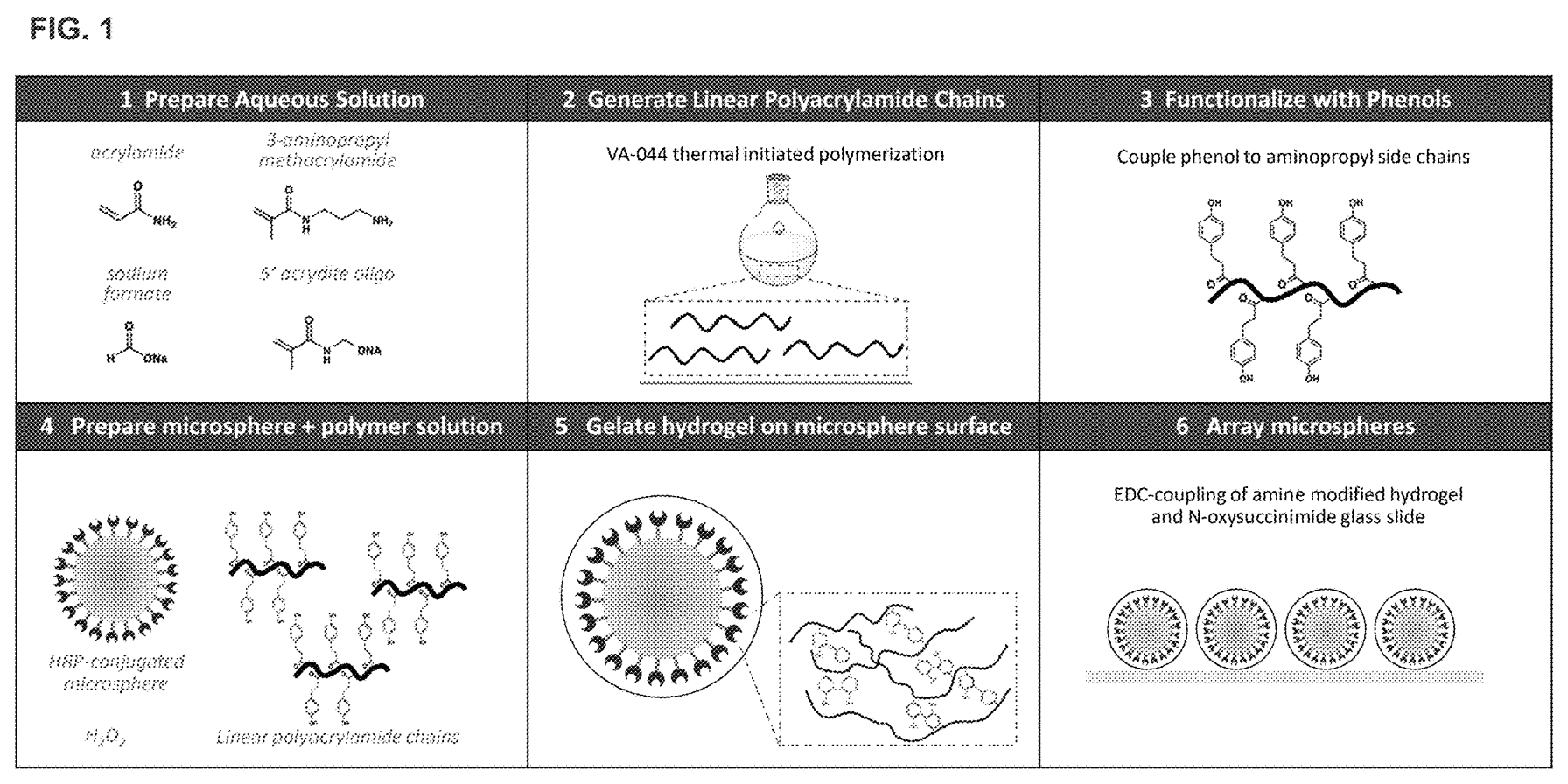

FIG. 1 schematically illustrates various steps pertaining to the horseradish peroxidase (HRP)-mediated surface gelation of microspheres, in accordance with the present disclosure.

FIG. 2 schematically illustrates various steps pertaining to surface gelation of microspheres using Particle Templated Emulsification (PTE).

DETAILED DESCRIPTION OF THE DISCLOSURE

Figure 3:
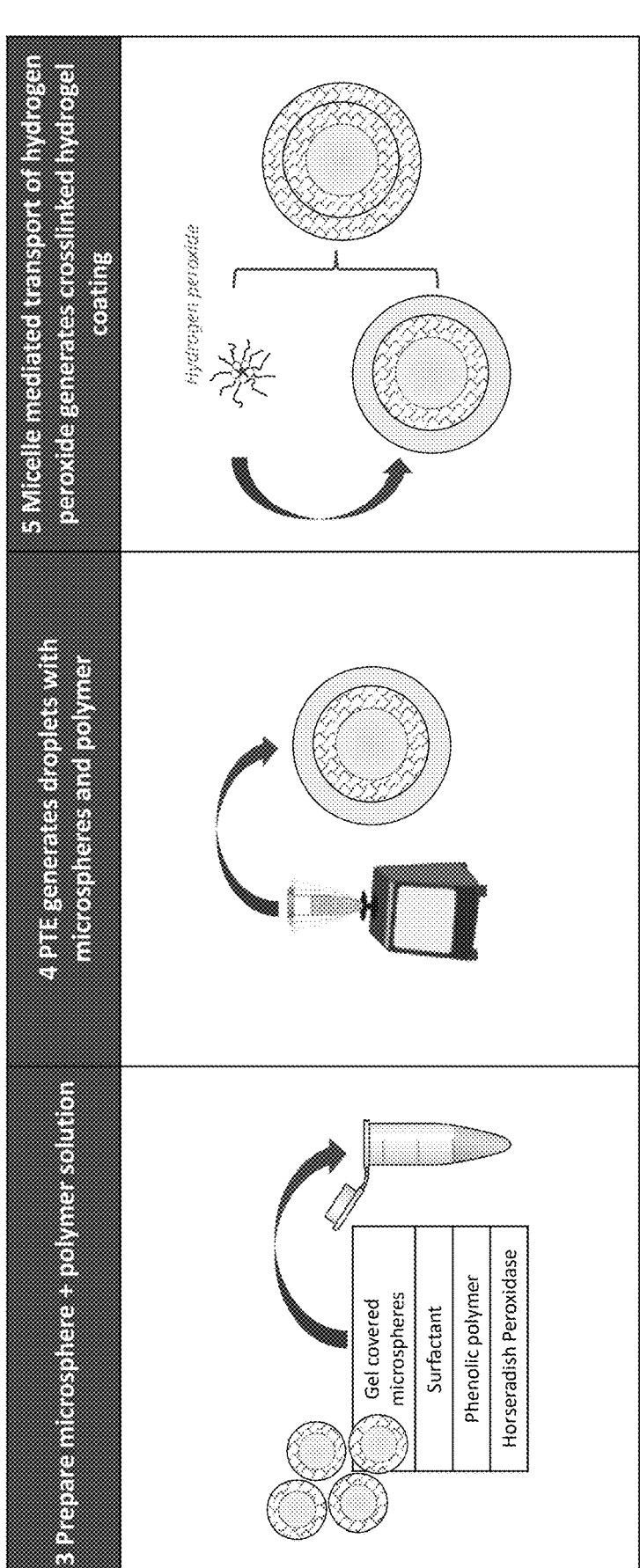
FIG. 3 schematically illustrates an aspect of the current disclosure in which steps 3-5 of FIG. 2 are repeated to optionally generate a thicker or multilayered hydrogel coating on features.

The present disclosure generally relates to, inter alia, compositions and methods for enhancing the sensitivity of spatial transcriptomics platforms. In particular, the disclosure relates to compositions and methods for increasing the capture probe loading capacity of features used to capture analytes in the spatial profiling of biological analytes. Some embodiments of the disclosure provide methods for generating a hydrogel coating on the surface of features (e.g. solid spherical beads, microspheres, etc.) using, for example, horseradish peroxidase (HRP)-mediated gelation. Some embodiments of the disclosure provide methods for generating a hydrogel coating on the surface of features by HRP-mediated gelation and Particle Templated Emulsification (PTE). The present disclosure also provides hydrogel-coated features having larger surface area and increased capture probe loading capacity, as well as arrays and substrates including the hydrogel-coated features.

Spatial transcriptomic systems can involve the transfer and capture of cellular transcripts, or proxies thereof, from biological samples (e.g. thin tissue sections) onto barcoded capture probes (e.g. polynucleotides or oligonucleotides). The capture probe may be immobilized on features that may take a variety of forms including, for example, solid, spherical beads (microspheres). Microspheres offer the advantage of highly uniform size distribution and are available in a range of sizes (e.g., micrometer scale) and materials. Solid microsphere surfaces, however, have limited capture probe loading capacity that may be too low to support spatial assays at the desired sensitivity. Increasing the surface area or volume available on the microspheres enhances their loading capacity. For example, coating the microsphere in a layer of hydrogel polymer significantly increases the microsphere's capture probe loading capacity.

Besides the increased loading capacity, another advantage for creating a hydrogel coating on the surface of a feature, in accordance with the current disclosure, pertains to the optical properties that may be afforded. Imaging tissue sections on arrays of small ~1 μm microspheres offers good image quality, but larger ~5 μm microspheres can distort the tissue image or the images of cellular content therein (e.g., neurons). Coating small microspheres (e.g., 1 μm) in a layer of optically transparent hydrogel to achieve, for example, a 5 μm feature size without sacrificing tissue image quality is advantageous.

Another advantage for creating a hydrogel coating on the surface of a feature, according the methods of the disclosure, is that the soft interface on the hydrogel microsphere aids in their attachment to surfaces as compared to solid beads.

As will be discussed in more detail below, the present disclosure provides a strategy to enhance the sensitivity of spatial transcriptomic assays and methods for increasing the loading capacity of features employed in said assays without sacrificing the quality of images taken of the features.

An example of a workflow for the approaches disclosed herein can begin with the preparation of an aqueous solution of a monomer mixture including acrylamide, 5' acrydite oligonucleotide, N-(3-aminopropyl)methylacrylamide HCl, and sodium formate. Polymerization of linear polyacrylamide chains is then thermally initiated with a polymerization initiator. The polymer is then functionalized, by phenol, for example. The functionalization with phenol can involve coupling phenol to aminopropyl side chains. Horseradish Peroxidase (HRP)-conjugated microspheres are then suspended in an aqueous solution containing the phenol functionalized polyacrylamide polymers, in the presence of hydrogen peroxide. In the presence of hydrogen peroxide and HRP-conjugated micropsheres, the phenolic groups in the polymer crosslink to form a hydrogel.

Another example of a workflow for the approaches disclosed here can begin by preparing an aqueous monomer mixture with acrylamide, 5' acrydite oligonucleotide, and sodium formate, then thermally initiating the polymerization of linear polyacrylamide chains with a polymerization initiator, followed by dialyzing the polymer to recover polyacrylamide chains of the desired length, and then functionalizing the polyacrylamide (e.g., with phenol). Microspheres may be suspended in an aqueous solution containing the functionalized polyacrylamide polymer, an enzyme (e.g., HRP) and a surfactant. Then, partitioning oil is added, and the sample is agitated (e.g., via vortexing) to partition the microspheres with the hydrogel polymer in the oil using Particle templated emulsification (PTE). PTE uses particles such as microspheres, oil, and a means of agitation (e.g., vortexer) to rapidly emulsify large volumes into monodisperse droplets. Once the microspheres are encapsulated, the substrate for the enzyme (e.g., hydrogen peroxide) is added. The substrate (e.g., hydrogen peroxide) can be delivered to the aqueous partitions via micelle mediated transport. In the presence of the enzyme and the enzyme substrate (e.g., hydrogen peroxide and HRP), the phenolic groups in the polymer crosslink to form a hydrogel coating around the microsphere.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

A "capture probe" when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

The term "barcode" is used herein to refer to a label, or identifier, that conveys or is capable of conveying information (e.g., information about an analyte in a sample, a bead, and/or a nucleic acid barcode molecule). A barcode can be part of an analyte or nucleic acid barcode molecule, or independent of an analyte or nucleic acid barcode molecule. A barcode can be attached to an analyte or nucleic acid barcode molecule in a reversible or irreversible manner. A particular barcode can be unique relative to other barcodes. Barcodes can have a variety of different formats. For example, barcodes may include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for or facilitates identification and/or quantification of individual sequencing-reads. In some embodiments, a barcode can be configured for use as a fluorescent barcode. For example, in some embodiments, a barcode can be configured for hybridization to fluorescently labeled oligonucleotide capture probes. Barcodes may be configured to spatially resolve molecular components found in biological samples, for example, at single-cell resolution (e.g., a barcode can be or can include a "spatial barcode"). In some embodiments, a barcode includes two or more sub-barcodes that together function as a single barcode. For example, a polynucleotide barcode may include two or more polynucleotide sequences (e.g., sub-barcodes). In some embodiments, the two or more sub-barcodes are separated by one or more non-barcode sequences. In some embodiments, the two or more sub-barcodes are not separated by non-barcode sequences.

The terms "cell", "cell culture", "cell line" refer not only to the particular subject cell, cell culture, or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the originally cell, cell culture, or cell line.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. In some embodiments, the term "about" indicates the designated value ±up to 10%, up to ±5%, or up to ±1%.

It is understood that aspects and embodiments of the disclosure described herein include "comprising", "consisting", and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Headings, e.g., (a), (b), (i) etc., are presented merely for ease of reading the specification and claims. The use of headings in the specification or claims does not require the steps or elements be performed in alphabetical or numerical order or the order in which they are presented.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, the use of these terms in the specification does not by itself connote any required priority, precedence, or order.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Compositions of the Disclosure

Features

The compositions described herein include hydrogel-coated features or a plurality of hydrogel-coated features, which are designed and/or configured to act as supports or repositories for various molecular entities used in sample analysis.

The hydrogel-coated features may be formulated into various shapes and dimensions depending on the context of intended use. Examples of features include, but are not limited to, a bead, a spot of any two- or three-dimensional geometry (e.g., an ink jet spot, a masked spot, a square on a grid), a well, and a hydrogel pad. The bead may be a core/shell bead that comprises an inner core (e.g. a microsphere or solid particle) and an outer shell (e.g., a hydrogel coating the microsphere).

In some embodiments of the present disclosure, the hydrogel-coated features are formulated as beads. In some embodiments provided herein, each of the hydrogel-coated features includes a solid particle that is encapsulated by the hydrogel. In some embodiments, the solid particle may be a microsphere. In some embodiments, the solid particle may include a silica inner core. In some embodiments, the microsphere may include polystyrene, carboxyl-modified polystyrene, polystyrene/2% divinylbenzene, polystyrene/10% divinylbenzene, polystyrene/55% divinylbenzene, or polymethyl methacrylate. In some embodiments, the solid particle may be modified by one or more of silane deposition and polymer adsorption.

In some embodiments, the solid particles (e.g., a population of solid particles) may have an average diameter of about 0.1 micrometer (micron) to about 50 micrometers. In some embodiments, the solid particles may have an average diameter of about 0.1 micrometer (micron) to about 100 micrometers. In some embodiments, the solid particles may have an average diameter of about 0.1 micrometer, about 0.2 micrometers, about 0.3 micrometers, about 0.4 micrometers, about 0.5 micrometers, about 0.6 micrometers, about 0.7 micrometers, about 0.8 micrometers, or about 0.9 micrometers. In some embodiments, the solid particles may have an average diameter of about 1 micron, about 2 micrometers, about 3 micrometers, about 4 micrometers, about 5 micrometers, about 6 micrometers, about 7 micrometers, about 8 micrometers, about 9 micrometers, about 10 micrometers, about 11 micrometers, about 12 micrometers, about 13 micrometers, about 14 micrometers, about 15 micrometers, about 16 micrometers, about 17 micrometers, about 18 micrometers, about 19 micrometers, about 20 micrometers, about 25 micrometers, about 30 micrometers, about 35 micrometers, about 40 micrometers, about 45 micrometers, about 50 micrometers, about 60 micrometers, about 70 micrometers, about 80 micrometers, about 90 micrometers, about 100 micrometers or any other values in between.

In some embodiments, the solid particle may have a diameter of about 0.1 micrometer to about 5 micrometers, about 1 micrometer to about 10 micrometers, about 1 micrometer to about 20 micrometers, about 1 micrometer to about 30 micrometers, about 1 micrometer to about 40 micrometers, about 1 micrometer to about 50 micrometers, about 1 micrometer to about 60 micrometers, about 1 micrometer to about 70 micrometers about 1 micrometer to about 80 micrometers about 1 micrometer to about 90 micrometers about 1 micrometer to about 100 micrometers or any other ranges in between.

In some embodiments of the disclosure (described in detail below), the features are coated with a hydrogel layer in repeated steps wherein every step adds a thickness of about 1 micrometer to about 20 micrometers. In some embodiments, the total thickness of the hydrogel encapsulating the feature (e.g., a multilayered hydrogel) is in the range of about 1 micrometer to about 100 micrometers.

In some embodiments, the hydrogel-coated features may have an average diameter of about 1 micron to about 100 micrometers. In some embodiments, the hydrogel-coated features may have an average diameter of about 1 micrometer, about 2 micrometers, about 3 micrometers, about 4 micrometers, about 5 micrometers, about 6 micrometers, about 7 micrometers, about 8 micrometers, about 9 micrometers, about 10 micrometers, about 11 micrometers, about 12 micrometers, about 13 micrometers, about 14 micrometers, about 15 micrometers, about 16 micrometers, about 17 micrometers, about 18 micrometers, about 19 micrometers, about 20 micrometers, about 25 micrometers, about 30 micrometers, 35 micrometers, about 40 micrometers, about 45 micrometers, about 50 micrometers, about 55 micrometers, about 60 micrometers, about 65 micrometers, about 70 micrometers, about 75 micrometers, about 80 micrometers, about 85 micrometers, about 90 micrometers, about 95 micrometers, about 100 micrometers or any other values in between.

The hydrogel-coated features of the disclosure may have an increased surface area and as such, may have a higher loading capacity for capture probes relative to uncoated features. The hydrogel-coated features may include a plurality of capture probes at an average density of about 500 to about 100,000 capture probes per micrometer$^2$. In some embodiments, the average density is about 1,000 to about 100,000 capture probes per micrometer$^2$. In some embodiments, the average density is about 10,000 to about 80,000 capture probes per micrometer$^2$. In some embodiments, the average density is about 25,000 to about 60,000 capture probes per micrometer$^2$.

In some embodiments, the hydrogel-coated features may include a plurality of capture probes at an average density of at least about 500 molecules per $\mu m^2$, at least about 1000 molecules per $\mu m^2$, at least about 1500 molecules per $\mu m^2$, at least about 2000 molecules per $\mu m^2$, at least about 5000 molecules per $\mu m^2$, at least about 10,000 molecules per $\mu m^2$, at least about 15,000 molecules per $\mu m^2$, at least about 20,000 molecules per $\mu m^2$, at least about 25,000 molecules per $\mu m^2$, at least about 30,000 molecules per $\mu m^2$, at least about 35,000 molecules per $\mu m^2$, at least about 40,000 molecules per $\mu m^2$, at least about 45,000 molecules per $\mu m^2$, at least about 50,000 molecules per $\mu m^2$, at least about 55,000 molecules per $\mu m^2$, at least about 60,000 molecules per $\mu m^2$, at least about 65,000 molecules per $\mu m^2$, at least about 70,000 molecules per $\mu m^2$, at least about 75,000 molecules per $\mu m^2$, at least about 80,000 molecules per $\mu m^2$, at least about 85,000 molecules per $\mu m^2$, at least about 90,000 molecules per $\mu m^2$, at least about 95,000 molecules per $\mu m^2$, at least about 100,000 molecules per $\mu m^2$, or any value in between.

In some embodiments, the hydrogel encapsulating the solid particles, may include a crosslinked polymer and a plurality of moieties produced by the methods of the disclosure, as described hereinafter. In some embodiments, the moiety is an organic functional group or may include a side chain that may have an organic functional group. In some embodiments, the organic functional group is an amine group. In some embodiments, the organic functional group is phenol. In some embodiment, the hydrogel may include an acrylamide copolymer. In some embodiments, the acrylamide copolymer is prepared from acrylamide and 3-aminopropyl methacrylamide monomers. In some embodiments, the acrylamide copolymer is prepared from acrylamide, 3-aminopropyl methacrylamide monomers, and 5' acrydite oligonucleotide monomers as described in more details below. In some embodiments, the acrylamide copolymer is prepared in the presence of sodium formate. In some embodiments, the hydrogel is prepared in the presence of a polymerization initiator. In some embodiments, the polymerization initiator is a water-soluble azo polymerization initiator. A non-limiting example of the water-soluble azo polymerization initiator includes VA-044.

In some embodiments, the hydrogel may include a cleavable functionality wherein the hydrogel can be degraded by cleavage of the cleavable functionality. In some embodiments, the crosslinks between chains of the linear polymer in the hydrogel may include the cleavable functionality.

In some embodiments, some or all the features of the disclosure are functionalized for analyte capture. For example, the features may include capture probes (e.g., capture probes) for analyte capture. A skilled artisan in the art will understand that the term capture probe generally refers to any molecule capable of capturing (directly or indirectly) and/or labelling an analyte of interest in or from a biological sample. In some embodiments, the capture probes may include a nucleic acid binding moiety (NABM), which can be small molecules, proteins, or oligonucleotides. In some embodiments, the capture probes may include ribonucleotides and/or deoxyribonucleotides as well as synthetic nucleotide residues that are capable of participating in Watson-Crick type or analogous base pair interactions. In some embodiments, the capture probes may include a conjugate (e.g., an oligonucleotide-antibody conjugate).

Capture Probes (Capture or Polynucleotide Capture Probes)

The features of the disclosure may include a plurality of capture probes. The capture probes of the disclosure may be directly or indirectly attached, incorporated, embedded, and/or affixed to the features. In some embodiments, the capture probe is attached to a moiety of the plurality of moieties within the hydrogel encapsulating the features.

In some embodiments, the capture probe may include a barcode sequence (e.g., a spatial barcode) and/or a capture domain. The capture domain may include a nucleic acid sequence (e.g., a poly(T) sequence) capable of binding to a poly(A) sequence of a nucleic acid, e.g., a poly(A) tail of an mRNA and/or to a poly(A) homopolymeric sequence present in genomic DNA, or a proxy thereof, such as a ligated probe pair. In some embodiments, a homopolymeric sequence is added to an mRNA molecule or a genomic DNA molecule using a terminal transferase enzyme to produce an analyte that has a poly(A) or poly(T) sequence. For example, a poly(A) sequence can be added to an analyte (e.g., a fragment of genomic DNA) thereby making the analyte capable of capture by a poly(T) capture domain. In some embodiments, a capture domain includes a poly(T) sequence, a random sequence, a gene specific sequence, a degenerate sequence, or a combination thereof.

In some embodiments, the capture probe may include a unique molecular identifier (UMI). UMIs can be used for determining the degree of gene expression of the captured analyte as described below in more detail.

Each capture probe can optionally include at least one cleavage domain. The cleavage domain represents the portion of the capture probe that is used to reversibly attach the capture probe to a feature. Further, one or more segments or regions of the capture probe can optionally be released from the feature by cleavage of the cleavage domain. As an example, spatial barcodes and/or universal molecular identifiers (UMIs) can be released by cleavage of the cleavage domain. In some embodiments, the capture probe may be optionally coupled to a feature by a cleavage domain, such as a disulfide linker, an enzyme cleavable linker, or a photo-induced cleavable linker.

In some embodiments, a cleavage domain is absent from the capture probe. Examples of substrates with attached capture probes lacking a cleavage domain are described for example in Macosko et al., (2015) Cell 161, 1202-1214.

In some embodiments, each capture probe of the disclosure may optionally include at least one, at least two, a least three, or at least four functional domains or regions. Each functional domain or region generally includes a functional nucleotide sequence for a downstream analytical step in the overall analysis procedure. For example, a capture probe of the disclosure can include (i) a sequencing domain, (ii) a PCR adaptor, and/or (iii) a capture region or capture domain capable of capturing (e.g., via binding) a target analyte or proxy thereof.

In some embodiments, the capture probe can include adapters that are useful for subsequent downstream processing. Examples of such as an adapter include a sequencer specific flow cell attachment sequence, e.g., a P5 sequence and/or a P7 sequence, as well as sequencing primer sequences, e.g., a Read 1 (R1) primer binding site and/or a Read 2 (R2) primer binding site.

Spatial Barcodes

In general, the spatial barcode of the disclosure includes a contiguous nucleic acid segment or at least two non-contiguous nucleic acid segments that function as a label or identifier that conveys or is capable of conveying spatial information. In some embodiments, a capture probe can include a spatial barcode that possesses a spatial aspect, where the spatial barcode is associated with a particular location within an array or a particular location on a substrate. In some embodiments, the spatial barcode is uniquely associated with a feature which is uniquely associated with a particular location within an array or a particular location on a substrate. A spatial barcode can be incorporated within the capture probe for use in barcoding a target analyte. In some embodiments, the functional sequences of a barcode can generally be designed or selected for compatibility with any of a variety of different sequencing systems, e.g., 454 Sequencing, Ion Torrent Proton or PGM, Illumina sequencing instruments, PacBio, Nanopore, etc., and the requirements thereof. In some embodiments, functional sequences can be designed or selected for compatibility with non-commercialized sequencing systems. Further, in some embodiments, functional sequences can be selected for compatibility with other sequencing systems, including non-commercialized sequencing systems.

A spatial barcode may be part of an analyte, or independent from an analyte (e.g., part of the capture probe). A spatial barcode can be a tag attached to an analyte (e.g., a nucleic acid molecule) or a combination of a tag in addition to an endogenous characteristic of the analyte (e.g., size of the analyte).

In some embodiments, the spatial barcode can be common to all of the capture probes attached to a given feature (e.g., the spatial barcode is unique to a feature on the array). In some embodiments, a spatial barcode can be unique. In some embodiments where the spatial barcode is unique, the spatial barcode can function both as a spatial barcode and as a unique molecular identifier (UMI), associated with one particular capture probe. In some embodiments, the spatial barcode and UMI are separate nucleic acid sequences and their functions within a capture probe do not overlap.

Spatial barcodes can have a variety of different formats. For example, spatial barcodes can include polynucleotide spatial barcodes, random nucleic acid and/or amino acid sequences, and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA before, during, and/or after downstream analyses (e.g., sequencing) of the analyte. In some embodiments, a spatial barcode is designed or selected to allow for identification and/or quantification of individual sequencing-reads. In some embodiments, a spatial barcode is used as a fluorescent barcode for which fluorescently labeled oligonucleotide capture probes hybridize and/or attach to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

In instances where multiple capture probes are attached to a feature, one or more spatial barcode sequences of the multiple capture probes can include sequences that are the same for all capture probes coupled to the feature, and/or sequences that are different across all capture probes coupled to the feature.

In some embodiments, capture probes attached to a single feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another array. In some embodiments, the identical spatial barcode sequences can be different from spatial barcode sequences of capture probes attached to another feature.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single feature. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular feature.

Capture Domains

A capture probe of the disclosure can include at least one capture domain. The "capture domain" can be an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence configured to interact with one or more analytes, such as one or more different types of nucleic acids (e.g., RNA and DNA). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence. In some embodiments, poly(T) sequences are configured to interact with messenger RNA (mRNA) molecules via the poly(A) tail of an mRNA transcript. In some embodiments, poly(T) sequences are configured to interact with a target nucleic acid (e.g., an RTL probe) via a poly(A) sequence contained within the target nucleic acid. In some embodiments, the functional nucleic acid sequence is the binding target of a protein (e.g., a transcription factor, a DNA binding protein, or a RNA binding protein), where the analyte of interest is a protein.

In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface capture probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single-stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide sequence. In some embodiments, a capture domain captures (e.g., hybridizes to) a splint oligonucleotide.

In some embodiments, the capture domain is located at the 3' end of the capture probe and includes a free 3' end that can be extended, e.g., by template dependent polymerization, to form an extended capture probe as described herein. In some embodiments, the capture domain includes a nucleotide sequence that is capable of hybridizing to nucleic acid, e.g., RNA or other analyte, present in the cells of the biological sample contacted with the array. In some embodiments, the capture domain can be selected or designed to hybridize selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, e.g., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, 20, 21, 22, 23, 24, 25, 26, 27, 28, 29, or 30 nucleotides. In some embodiments, the capture domain includes at least 25, 30, or 35 nucleotides.

In some embodiments, random sequences, e.g., random hexamers, decamers, or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" capture probe). This can, for example, be located 5' or 3' of the poly(T) sequence, e.g., at the 3' end of the capture domain. The poly(T)-random sequence capture probe can facilitate capture of the mRNA poly(A) tail. In some embodiments, the capture domain can be an entirely random sequence. In some embodiments, degenerate capture domains can be used.

The capture domain can be based on a particular gene sequence or particular motif sequence or common/conserved sequence, that it is designed to capture (e.g., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, Rnase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended analyte. In some embodiments, an anchor sequence includes a sequence of nucleotides, including a 1-mer, 2-mer, 3-mer or longer sequence. In some embodiments, the anchor sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN, where V can be A or C or G, and N can be A or T or C or G. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes may be used when the nucleic acids in the biological sample are modified prior to capture on the array. In some embodiments, the blocking probe is used to block or modify the free 3' end of the capture domain. In some embodiments, blocking probes can be hybridized to the capture probes to mask the free 3' end of the capture domain, e.g., hairpin probes, partially double stranded probes, or complementary sequences. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3' Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the target nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, e.g., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

Unique Molecular Identifiers (UMI)

The capture probes of the disclosure can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can include one or more specific polynucleotides sequences, one or more random nucleic acid and/or amino acid sequences, and/or one or more synthetic nucleic acid and/or amino acid sequences.

In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial part (e.g., 80% or more) of the nucleic acid molecules in the biological sample. These nucleotides can be completely contiguous, e.g., in a single stretch of adjacent nucleotides, or they can be separated into two or more separate subsequences that are separated by 1 or more nucleotides.

In some embodiments, a UMI is attached to an analyte in a reversible or irreversible manner. In some embodiments, a UMI is added to, for example, a fragment of a DNA or RNA sample before or during, sequencing of the analyte. In some embodiments, a UMI allows for identification and/or quantification of individual sequencing-reads. In some embodiments, a UMI is used as a fluorescent barcode for which fluorescently labeled oligonucleotide probes hybridize to the UMI. Functionally, UMIs allow for demultiplexing of sequencing reads and biases that may be introduced through downsstream processing (e.g., PCR amplification). For example, each biomolecule captured by a capture probe on a feature of a spatial array should contain a distinct UMI that is distinguishable from other UMIs on the spatial array. Typically, if two or more sequencing reads contain the same UMI, they are discarded or filtered from the data set.

Arrays

In some embodiments of the compositions and methods described herein, features are collectively positioned on a substrate to form an array. In such an array, a specific arrangement of a plurality of features is either irregular or forms an ordered pattern. Individual features on the array differ from one another based on their relative spatial locations. In some embodiments, a plurality of the features of the disclosure are spatially ordered in an array and each feature of the plurality of the features is associated with a unique spatial location on the array.

In some embodiments, the hydrogel-coated features of the disclosure (e.g., amine modified) are arrayed via EDC-coupling on N-oxysuccinmide glass slides.

In some embodiments, the arrays of the disclosure are designed to accommodate a large number of features. For example, the array can include at least 5,000 features, for examples at least 10,000 features, at least 20,000 features, at least 50,000 features, at least 100,000 features, at least 500,000 features, at least 1,000,000 features, at least 2,000,000 features, at least 5,000,000 features, or at least 10,000,000 features. In some embodiments, the plurality of features includes a single type of feature (e.g., substantially uniform in volume, shape, and other physical properties, such as translucence). In some embodiments, the plurality of features includes two or more types of different features.

Substrates

Provided in the present disclosure are substrates on which hydrogel-coated features are immobilized. A substrate may be designed and/or configured to function as a support for direct or indirect attachment of the features of the disclosure.

Features may be directly or indirectly attached, embedded, or affixed to a substrate. In some embodiments, the features are not directly or indirectly attached embedded, or affixed to a substrate, but instead, for example, are disposed within an enclosed or partially enclosed three-dimensional space (e.g., wells or divots).

Substrates of the disclosure can be formed from a variety of solid materials, gel-based materials, colloidal materials, semi-solid materials (e.g., materials that are at least partially cross-linked), materials that are fully or partially cured (e.g., via photolithography), and materials that undergo a phase change or transition to provide physical support. Substrates of the disclosure can be insoluble in aqueous liquid.

Examples of suitable substrates of the disclosure include, but are not limited to, slides (e.g., slides formed from various glasses, slides formed from various polymers), layers and/or films, membranes (e.g., porous membranes), flow cells, cuvettes, wafers (e.g., silicon), plates, or combinations thereof.

In some embodiments, the hydrogel-coated features of the disclosure are arrayed with EDC-coupling to the substrate. In some embodiments, the hydrogel-coated features of the disclosure are arrayed with EDC-coupling on N-oxysuccinimide glass slides.

In some embodiments, substrates can optionally include functional elements such as recesses, protruding structures, microfluidic elements (e.g., channels, reservoirs, electrodes, valves, seals), and various markings.

A substrate can generally have any suitable form or format. For example, a substrate can be flat, curved, e.g., convexly or concavely curved towards the area where the interaction between the substrate and a biological sample, e.g., tissue sample, takes place. In some embodiments, a substrate is flat, e.g., planar, chip, or slide. In some embodiments, a substrate can contain one or more patterned surfaces within the substrate (e.g., channels, wells, projections, ridges, divots, hydrophobically defined spaces intra hydrophillically defined spaces, etc.).

Substrates of the disclosure can be of any desired shape. For example, a substrate can be generally a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip or a slide such as a microscope slide).

In some embodiments of the disclosure, substrates can optionally include various structures such as, but not limited to, projections, ridges, and channels. A substrate can be micro-patterned to limit lateral diffusion (e.g., to prevent overlap of spatial barcodes or barcoded features). A substrate including such structures can be modified to allow association of analytes, features (e.g., beads), or capture probes at individual sites or regions. For example, the sites or regions where a substrate is modified with various structures can be contiguous or non-contiguous with other sites or regions.

In some embodiments, the surface of a substrate can be modified so that discrete sites or regions are formed that can only have or accommodate a specific number of features, for example, a single feature. In some embodiments, the surface of a substrate can be modified so that features adhere to random sites or regions. In some embodiments, the surface of a substrate can be modified so that features are substantially regularly spaced from one another on the substrate.

In some embodiments, the surface of a substrate is modified to contain one or more wells, using techniques such as (but not limited to) stamping, microetching, photolithography, or molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments where the substrate is modified to contain one or more structures, including but not limited to, wells, sites, spots, projections, ridges, features, or markings, the structures can include physically altered sites or regions. For example, a substrate modified with various structures can include physical properties, including, but not limited to, physical configurations, magnetic or compressive forces, chemically functionalized sites, chemically altered sites, and/or electrostatically altered sites. In some embodiments where the substrate is modified to contain various structures (e.g., wells, sites, spots, projections, ridges, features, or markings), the structures are applied in a pattern. In some embodiments, the structures can be randomly distributed. In some embodiments, the structures can be regularly spaced from one another on the substrate. In some embodiments, the structures can be substantially regularly spaced from one another on the substrate.

A wide variety of different substrates can be used for the compositions and methods of the disclosure. In general, a substrate can be any suitable support material. Exemplary substrates include, but are not limited to, glass, modified and/or functionalized glass, films, membranes, plastics (e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene polycarbonate, or combinations thereof. In some preferred embodiments, the substrates can include glass, silicon dioxide or a silicon wafer.

In some embodiments, the substrate is a conductive substrate. Conductive substrates (e.g., electrophoretic compatible arrays) generated as described herein can be used in the spatial detection of analytes. For example, an electrophoretic field can be applied to facilitate migration of analytes towards the barcoded features (e.g., features immobilized on paper, features immobilized in a hydrogel film, or features immobilized on a glass slide having a conductive coating). In some embodiments, a conductive substrate can include glass (e.g., a glass slide) that has been coated with a substance or otherwise modified to confer conductive properties to the glass.

Kits

Further provided herein are kits for the practice of a method described herein. In some embodiments, provided herein are kits for the spatial analysis of a biological analyte in a biological sample. In some embodiments, the kits are for the spatial analysis of a nucleic acid analyte (e.g. mRNA, gDNA, RNA, or tRNA) and/or a protein analyte. Such kits can include one or more substrates including the hydrogel-coated features of the disclosure. In some embodiments, a kit can further include instructions for using the components of the kit to practice a method described herein.

In some embodiments, the components of a kit can be in separate containers. In some other embodiments, the components of a kit can be combined in a single container. Accordingly, in some embodiments, the kit includes fixatives for fixing the biological sample. In some embodiments, the fixatives are ethanol, methanol, acetone, formaldehyde, paraformaldehyde-Triton, glutaraldehyde, and combinations thereof. In some embodiments, the kit includes staining reagents for staining the biological sample (e.g., eosin and/or hematoxylin). In some embodiments, the kit includes a detectable label for use in staining the biological sample (e.g., a radioisotope, a fluorophore, a chemiluminescent compound, a bioluminescent compound, or a combination thereof).

In some embodiments, the kit can further include instructions for performing a disclosed method. The instructions for practicing the method are generally recorded on a suitable recording medium. For example, the instructions can be printed on a substrate, such as paper or plastic, etc. The instructions can be present in the kit as a package insert, in the labeling of the container of the kit or components thereof (e.g., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

Methods of the Disclosure

The disclosure provides, inter alia, methods for coating features (e.g., solid particles such as microspheres) in one or more layers of hydrogel polymers thereby generating hydrogel-coated features. In some aspects, the hydrogel is generated using horseradish peroxidase (HRP)-mediated gelation. In other aspects, the hydrogel is generated using horseradish peroxidase (HRP)-mediated gelation and Particle Templated Emulsification (PTE). PTE is an approach for generating compartmentalized reactions in monodispersed droplets with vortexing (Hatori et al., 2018). By vortexing a mixture of hydrogel particles and solid particles, the solid particles become encapsulated in monodispersed emulsions that are useful for most droplet applications. The particles afford an independent avenue for introducing compounds into the droplets, for example, by functionalizing with oligonucleotides, proteins, and reactive groups.

Methods For Preparing Hydrogel-Coated Features

As described in more detail below, one aspect of the disclosure relates to approaches and methods for preparing a hydrogel-coated feature. In some embodiments, the methods include (a) providing a solid particle; and (b) encapsulating the solid particle with a hydrogel comprising a crosslinked polymer and a plurality of moieties.

In some embodiments, each moiety of the plurality of moieties may include an oligonucleotide (e.g., a side chain that includes an oligonucleotide). In some embodiments, each moiety of the plurality of moieties may include an organic functional group (e.g., a side chain that has an organic functional group). In some embodiments, the functional group is an amine group. In some embodiments of the methods of the disclosure, the solid particle includes a plurality of a capture probe, wherein each capture probe is attached to a moiety of the plurality of moieties within the hydrogel. In some embodiments the moieties are succinimidyl moieties.

In some non-limiting embodiments, step (b) includes mixing the solid particle, a plurality of linear chains of the polymer wherein each linear chain includes a functional group, an enzyme, and a substrate for the enzyme, wherein the mixing is performed under conditions in which the enzyme or enzymatic activity thereof mediates crosslinking of the linear chains to produce a crosslinked polymer, thereby producing a hydrogel that encapsulates the solid particle.

In some embodiments, step (b) includes (i) mixing an aqueous suspension comprising the solid particle, a plurality of linear chains of the polymer wherein each linear chain comprises a functional group, an enzyme whose enzymatic activity is capable of crosslinking the functional group, and a surfactant with a partitioning oil, thereby creating an emulsion in which the solid particle, a plurality of the linear polymer chains, and the enzyme are partitioned into a droplet; and (ii) adding a substrate for the enzyme, under conditions in which the enzyme or enzymatic activity thereof mediates crosslinking of the linear polymer chains to produce the crosslinked polymer, thereby producing a hydrogel that encapsulates the solid particle.

In non-limiting embodiments, suitable surfactants include non-ionic surfactants, e.g., Triton X-100 and Tween-20.

Suitable oils include fluorinated oil, silicone oil, and hydrocarbon oil.

Polymers of the disclosure include water soluble polymers that possess moieties that are cross-linkable through enzymatic reactions mediated by an enzyme (e.g., HRP). Other polymers such as unmodified natural polysaccharides, derivatives of polysaccharides, proteins and synthetic polymers, alginates, polyvinyl alcohol-derivatives may be used. In some embodiments, the hydrogel may include an acrylamide copolymer. The acrylamide copolymer may be prepared from acrylamide and 3-aminopropyl methacrylamide monomers. In some embodiments, the acrylamide copolymer may be prepared from acrylamide, 3-aminopropyl methacrylamide, and 5' acrydite oligonucleotide monomers. In some embodiments, the acrylamide copolymer may be prepared in the presence of sodium formate.

In non-limiting examples, the enzyme may be a peroxidase, a transglutaminase, a tyrosinase, a laccase, a phosphatase, an oxidoreductase, or a metalloproteinase. Examples of substrates include hydrogen peroxide or hydroperoxides. In some embodiments, the peroxidase is horseradish peroxidase, and the substrate for the enzyme is hydrogen peroxide.

In some embodiments, the enzyme may be a peroxidase and/or the functional group may be a phenol, an acetylacetone, or a dihydrotetrazine group.

In some embodiments, the enzyme is attached to the feature, e.g., solid particle. In some embodiments, the enzyme is attached to the solid particle via a linking moiety. Non-limiting examples of a linking moiety includes, 5' acrydite oligos, or antibodies.

In some embodiments, the methods include repeating steps (i) and (ii) one or more times to encapsulate the solid particle with one or more additional layer(s) of hydrogel. In some embodiments, each of the one or more additional layer(s) contributes a thickness of about 1 micrometer to about 20 micrometers, optionally wherein the total thickness of the hydrogel surrounding the solid particle is in the range of about 1 micrometer to about 100 micrometers.

In some embodiments of the methods of preparing hydrogel coated features described above, the functional group may be phenol. HRP catalyzes the oxidative coupling of phenol resulting in polyphenols linked by C—O and C—C groups, via the consumption of hydrogen peroxide. In some embodiments, the phenol may be attached to the linear chain of the polymer via an amide coupling reaction.

In some embodiments of the methods of preparing hydrogel coated features described above, the hydrogel includes a cleavable functionality, wherein the hydrogel can be degraded by cleavage of the cleavable functionality. In some embodiments, the crosslinks between chains of the linear polymer in the hydrogel may include the cleavable functionality.

In some embodiments, the plurality of linear chains are selected after polymerization such that each linear chain in the plurality of linear chains is of a desired length. For example, polymerization of linear polyacrylamide chains can be initiated (e.g., thermally with VA-044) and the plurality of polymer chains is then dialyzed one or more times to recover polyacrylamide chains of a desired length. Next, the linear polyacrylamide chains are functionalized (e.g., phenol functionalized) and the resultant functionalized polymer chains can be further dialyzed one or more times. In some embodiments of the methods of the disclosure, each chain in the plurality of linear chains may conform to the molecular formula $(C_3H_5NO)_n$ wherein n is in the range of about 5-1000 (e.g., 5-50, 50-100, 100-500, 500-700, 700-1000).

In some embodiments, the capture probe may include a barcode sequence and a capture domain. In some embodiments, the capture domain may include a poly(T) sequence. In some embodiments, the capture probe may include a unique molecular identifier (UMI).

In some embodiments of the methods for preparing a plurality of hydrogel-coated features, the methods include: (a) suspending a plurality of features in an aqueous solution including a polymerizable monomer and a surfactant, thereby forming a suspension comprising the plurality of features; (b) adding a partitioning oil to the suspension and emulsifying the suspension into a plurality of droplets, wherein a droplet of the plurality of droplets includes a feature of the plurality of features coated with the polymerizable monomer; (c) contacting the plurality of droplets with a polymerization agent such that the polymerizable monomer coating a feature of the plurality of features is polymerized to form a plurality of hydrogel-coated features.

Methods of Immobilizing a Capture Probe on a Feature

The present disclosure provides methods for immobilizing a capture probe on a feature, the methods include: (a) encapsulating the feature with a hydrogel comprising a crosslinked polymer, and (b) attaching the capture probe to a moiety within the hydrogel.

In some embodiments, step (a) includes mixing the feature (e.g., a solid particle), a plurality of linear chains of the polymer wherein each linear chain includes a functional group, an enzyme, and a substrate for the enzyme, wherein the mixing is performed under conditions in which the enzyme mediates crosslinking of the linear chains to produce a crosslinked polymer, thereby producing a hydrogel that encapsulates the solid particle.

Non-limiting examples of enzymes include a peroxidase, a transglutaminase, a tyrosinase, a laccase, a phosphatase, an oxidoreductase, and a metalloproteinase. In some embodiments, the enzyme is horseradish peroxidase. In some embodiments the enzyme is attached to the feature (e.g. HRP-conjugated microspheres described above). In some embodiments, the substrate for the enzyme is hydrogen peroxide.

In some embodiments, step (a) includes mixing a solid particle conjugated to horseradish peroxidase with linear polyacrylamide chains functionalized with phenols in the presence of hydrogen peroxide $(H_2O_2)$ thereby gelating the hydrogel on the surface of the solid particle. In the presence of hydrogen peroxide and HRP, the phenolic groups in the polymers can undergo one-electron oxidation and generate reactive radical groups which subsequently react with each other to form the cross-linked hydrogel.

In some embodiments of the methods, step (a) includes (i) mixing an aqueous suspension including the feature, a plurality of linear chains of the polymer wherein each linear chain includes a functional group, an enzyme with enzymatic activity capable of crosslinking the functional group, and a surfactant with a partitioning oil, thereby creating an emulsion in which the solid particle, a plurality of the linear polymer chains, and the enzyme are partitioned into a droplet; and (ii) adding a substrate for the enzyme, under conditions in which the enzyme mediates crosslinking of the linear polymer chains to produce the crosslinked polymer, thereby producing a hydrogel that encapsulates the feature.

In some embodiments, the methods include repeating steps (i)-(ii) one or more times to encapsulate the feature with one or more additional layer(s) of hydrogel.

In some embodiments, the moiety may include an oligonucleotide (e.g., a side chain with an oligonucleotide), and step (b) includes hybridizing the capture probe to the oligonucleotide. In some embodiments, a portion of the capture probe proximal to its 5' end, is hybridized to the moiety (e.g., the oligonucleotide).

In some embodiments, the moiety may include an organic functional group (e.g., a side chain with an organic functional group), and step (b) includes attaching the capture probe to the organic functional group. In some embodiments, a portion of the capture probe proximal to its 5' end, is attached to the organic functional group.

In some embodiments, the capture probe is immobilized on a feature via its 5' end. In some embodiments, the capture probe is immobilized on a feature via its 5' end and includes from the 5' to 3' end: one or more barcodes (e.g., a spatial barcode and/or a UMI) and one or more capture domains. In some embodiments, the capture probe is immobilized on a feature via its 5' end and includes from the 5' to 3' end: one barcode (e.g., a spatial barcode and/or a UMI) and one capture domain. In some embodiments, the capture probe is immobilized on a feature via its 5' end and includes from the 5' to 3' end: a functional domain, one or more barcodes (e.g., a spatial barcode and/or a UMI), and a capture domain. In some embodiments, the capture probe is immobilized on a feature via its 5' end and includes from the 5' to 3' end: a cleavage domain, a functional domain, one or more barcodes (e.g., a spatial barcode and/or a UMI), and a capture domain.

In some embodiments, the capture probe is immobilized on a feature via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a feature via its 5' end and includes from the 5' to 3' end: a cleavage domain, a functional domain, a spatial barcode, a UMI, and a capture domain. In some embodiments, the capture probe is immobilized on a feature via its 5' end and does not include a spatial barcode. In some embodiments, the capture probe is immobilized on a feature via its 5' end and does not include a UMI. In some embodiments, the capture probe includes a sequence for initiating a sequencing reaction.

In some embodiments, the capture probe is immobilized on a feature via its 3' end. In some embodiments, the capture probe is immobilized on a feature via its 3' end and includes from the 3' to 5' end: one or more barcodes (e.g., a spatial barcode and/or a UMI) and one or more capture domains. In some embodiments, the capture probe is immobilized on a feature via its 3' end and includes from the 3' to 5' end: one barcode (e.g., a spatial barcode or a UMI) and one capture domain. In some embodiments, the capture probe is immobilized on a feature via its 3' end and includes from the 3' to 5' end: a functional domain, one or more barcodes (e.g., a spatial barcode and/or a UMI), and a capture domain. In some embodiments, the capture probe is immobilized on a feature via its 3' end and includes from the 3' to 5' end: a cleavage domain, a functional domain, one or more barcodes (e.g., a spatial barcode and/or a UMI), and a capture domain. In some embodiments, the capture probe is immobilized on feature via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g., the functional group can be placed at the 5' or 3' end of the capture probe or within the sequence of the capture probe. In some embodiments, a capture probe can further include a substrate. A typical substrate for a capture probe to be immobilized includes moieties which are capable of binding to such capture probes, e.g., to amine-functionalized nucleic acids. Examples of such substrates are carboxy, aldehyde, or epoxy substrates.

Methods for Spatial Analysis of Biological Analytes in a Biological Sample

The present disclosure describes methods for enhancing the sensitivity of spatial transcriptomics systems and platforms. In one aspect the disclosure relates to methods for the spatial analysis of biological analytes in a biological sample including the hydrogel-coated features described herein.

In some embodiments, the disclosure provides methods for spatial analysis of a biological analyte in a biological sample, the methods include: (a) providing a hydrogel-coated feature of the disclosure; (b) contacting the hydrogel-coated feature or the substrate with a biological sample under conditions where the biological analyte, or a proxy thereof, binds (e.g., hybridizes) to the capture probe on the hydrogel-coated feature; and (c) determining (i) all or a part of the sequence of the biological analyte, or the proxy thereof, hybridized to the capture probe, or a complement thereof, and (ii) the sequence of the barcode, or a complement thereof, and using the determined sequence of (i) and (ii) to identify the location of the biological analyte in the biological sample.

In some embodiments of the methods for spatial analysis of the disclosure, the spatial resolution for the location of the biological analyte in the biological sample is increased as compared to a reference spatial resolution achieved using a corresponding method where the method comprises a feature that does not comprise a hydrogel.

Spatial Analysis

An exemplary workflow for the array-based spatial analysis methods disclosed herein involves the transfer of one or more analytes from a biological sample to an array of hydrogel-coated features on a substrate, where each hydrogel-coated feature is associated with a unique spatial location on the array. Subsequent analysis of the transferred analytes includes determining the identity of the analytes and the spatial location of each analyte within the biological sample. The spatial location of each analyte within the biological sample is determined based on the feature to which each analyte is bound on the array, and the feature's relative spatial location within the array.

In another example of a workflow, the biological analytes are proteins, in which case a set of analyte capture agents (e.g., antibody-oligonucleotide conjugates) is applied to the biological sample, and the capture probes bind to the oligonucleotide of the antibody-oligonucleotide conjugates after binding of the antibody-oligonucleotide conjugate to a target of interest (e.g., protein). In some instances, the oligonucleotide can be cleaved or otherwise released from the antibody prior to being captured by the capture probe. In other instances, the oligonucleotide is not cleaved from the antibody prior to being captured by the capture probe.

The spatial analysis of a biological analyte present in a biological sample may begin, for example, with digitally imaging a fresh or frozen tissue section for histological purposes and placing the tissue section on a device (e.g., array) containing capture probes that bind to one or more biological analytes in the sample. The tissue section can be fixed and permeabilized to release analytes which can be captured by capture probes disposed adjacent to the cells that the analytes are derived from, which allows for or facilitates downstream analytical application of the captured analytes (e.g., spatially determined gene expression or protein activity). In instances where the target analyte is a nucleic acid such as, for example mRNA, the captured nucleic acid or a nucleic acid derived therefrom (e.g., cDNA synthesized from captured RNA) is used for preparation of sequencing libraries. The libraries are sequenced, and sequencing data visualized to determine which genes are expressed, and where, as well as in what quantity, within a cell or tissue. In an example of a workflow, the cDNA generated from mRNA captured by capture probes disposed adjacent to a specific spot or region of the tissue sample generally share a common spatial barcode. Sequencing libraries are then generated from the cDNA and sequenced and the spatial barcodes are subsequently used to associate the sequencing reads back to the tissue section images for spatial gene expression analysis and mapping.

Another example of a workflow can include preparing a biological sample on a spatially-barcoded array. Sample preparation may include placing the sample on a slide, fixing the sample, and/or staining the biological sample for imaging. The stained sample can be imaged on the array using brightfield (to image the sample with, for example, a hematoxylin and/or eosin stain) and/or fluorescence (to image features comprising fluorescent moieties) modalities in such a way that positions in the spatially-barcoded array can be mapped to positions in the sample.

Optionally, the sample can be destained prior to permeabilization. In some embodiments, analytes are released from the sample and capture probes forming the spatially-barcoded array hybridize to the released analytes. The analyte-bound capture probes can be analyzed to determine the identity of the analyte and where it was located on the spatial array. Where the analyte is RNA (e.g., mRNA), the RNA can be reverse transcribed into cDNA containing information from the spatial barcode of the capture probe hybridized to the RNA, and an amplicon sequencing library can be prepared and sequenced to identify the RNA and where it was located on the spatial array. The mapping of positions on the spatially-barcoded array to positions in the sample can be used to provide information about the origin of the analyte in the sample.

Using the methods, and compositions described herein, RNA transcripts present in biological samples (e.g., tissue samples) can be used for spatial transcriptome analysis. In particular, in some cases, the barcoded oligonucleotides may be configured to prime, replicate, and consequently yield barcoded extension products from an RNA template, or derivatives thereof. For example, in some cases, the barcoded oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcoded oligonucleotides. Reverse transcriptases (RTs) can use an RNA template and a primer complementary to the 3' end of the RNA template to direct the synthesis of the first strand complementary DNA (cDNA). Many RTs can be used in this reverse transcription reactions, including, for example, avian myeloblastosis virus (AMV) reverse transcriptase, moloney murine leukemia virus (M-MuLV or MMLV), and other variants thereof. Some recombinant M-MuLV reverse transcriptase, such as, for example, PROTOSCRIPT® II reverse transcriptase, can have reduced RNase H activity and increased thermostability when compared to its wild type counterpart, and provide higher specificity, higher yield of cDNA and more full-length cDNA products with up to 12 kilobase (kb) in length. In some embodiments, the reverse transcriptase enzyme is a mutant reverse transcriptase enzyme such as, but not limited to, mutant MMLV reverse transcriptase. In another embodiment, the reverse transcriptase is a mutant MMLV reverse transcriptase such as, but not limited to, one or more variants described in US Patent Publication No. 20180312822.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture probe binding domain (e.g., a poly(A) sequence, a non-homopolymeric sequence). After hybridization to the analyte, a ligase (e.g., a T4 RNA ligase (Rnl2), a PBCV-1 DNA Ligase or Chorella virus DNA Ligase, a single-stranded DNA ligase, or a T4 DNA ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). In some instances, the ligation product is released using heat. In some instances, the ligation product is released using KOH. The released ligation product can then be captured by capture probes (e.g., instead of direct capture of an analyte) on an array, optionally amplified, and sequenced, thus determining the location and optionally the abundance of the analyte in the biological sample.

In a non-limiting example of templated ligation methods disclosed herein, after a biological sample is contacted with a substrate including a plurality of capture probes and contacted with (a) a first probe having a target-hybridization sequence and a primer sequence and (b) a second probe having a target-hybridization sequence and a capture probe binding domain (e.g., a poly-A sequence), the first probe and a second probe hybridize to an analyte. A ligase ligates the first probe to the second probe thereby generating a ligation product. The ligation product is released from the analyte by digesting the analyte using an endoribonuclease. The sample is permeabilized and the ligation product hybridizes to a capture probe on the substrate. Methods and composition for spatial detection using templated ligation have been described in PCT Publ. No. WO 2021/133849 A1, U.S. Pat. Nos. 11,332,790 and 11,505,828, each of which is incorporated by reference in its entirety.

In a non-limiting example of the workflows described above, a biological sample (e.g., tissue section), can be fixed with methanol, stained with hematoxylin and eosin, and imaged. Optionally, the sample can be destained prior to permeabilization. The images can be used to map spatial gene expression patterns back to the biological sample. A permeabilization enzyme can be used to permeabilize the biological sample directly on the slide. Analytes (e.g., poly-adenylated mRNA) released from the overlying cells of the biological sample can be captured by capture probes within a capture area on a substrate. Reverse transcription (RT) reagents can be added to permeabilized biological samples. Incubation with the RT reagents can produce spatially-barcoded cDNA from the captured analytes (e.g., polyade-nylated mRNA). Second strand reagents (e.g., second strand primers, template switch oligonucleotides, enzymes) can be added to the biological sample on the slide to initiate second strand synthesis. The resulting second cDNA can be dena-tured from the capture probe template and transferred (e.g., to a clean tube) for amplification, and/or library construc-tion. The spatially-barcoded, cDNA can be amplified via PCR prior to library construction. The cDNA can be enzy-matically fragmented and size-selected to optimize the cDNA amplicon size. P5, P7, i7, and i5 can be used as sample indexes, and TruSeq Read 2 can be added via End Repair, A-tailing, Adaptor Ligation, and PCR. The cDNA fragments can be sequenced using paired-end sequencing using TruSeq Read 1 and TruSeq Read 2 as sequencing primer sites (e.g., when utilizing Illumina based sequencers, other sequencing platforms may require different or addi-tional sequencing primer sequences).

In some embodiments, performing correlative analysis of data produced by this workflow, and other workflows described herein, can yield over 95% correlation of genes expressed across two capture areas (e.g., 95% or greater, 96% or greater, 97% or greater, 98% or greater, or 99% or greater).

In some embodiments, after cDNA is generated (e.g., by reverse transcription) the cDNA can be amplified directly on the substrate surface. Generating multiple copies of the cDNA (e.g., cDNA synthesized from captured analytes) via amplification directly on the substrate surface can improve final sequencing library complexity. Thus, in some embodi-ments, cDNA can be amplified directly on the substrate surface by isothermal nucleic acid amplification. In some embodiments, isothermal nucleic acid amplification can amplify RNA or DNA.

Any variety of staining and imaging techniques as described herein or known in the art can be used in accor-dance with methods described herein. In some embodi-ments, the staining includes optical labels as described herein, including, but not limited to, fluorescent, radioactive, chemiluminescent, calorimetric, or colorimetric detectable labels. In some embodiments, the staining includes a fluo-rescent antibody directed to a target analyte (e.g., cell surface or intracellular proteins) in the biological sample. In some embodiments, the staining includes an immunohisto-chemistry stain directed to a target analyte (e.g., cell surface or intracellular proteins) in the biological sample. In some embodiments, the staining includes a chemical stain such as hematoxylin and eosin (H&E) or periodic acid-schiff (PAS). In some embodiments, significant time (e.g., days, months, or years) can elapse between staining and/or imaging the biological sample and performing analysis. In some embodi-ments, reagents for performing analysis are added to the biological sample before, contemporaneously with, or after the array is contacted to the biological sample. In some embodiments, the method may include placing the array onto the biological sample. In some embodiments, the array is a flexible array where the plurality of spatially-barcoded hydrogel-coated features (e.g., with capture probes) are attached to a flexible substrate. In some embodiments, measures are taken to slow down a reaction (e.g., cooling the temperature of the biological sample or using enzymes that preferentially perform their primary function at lower or higher temperature (as compared to their optimal functional temperature) before the array is contacted with the biologi-cal sample. In some embodiments, analyzing the analyte may be without bringing the biological sample out of contact with the array. In some embodiments, analyzing the analyte is performed after the biological sample is no longer in contact with the array. In some embodiments, the biological sample is tagged with an analyte capture agent before, contemporaneously with, or after staining and/or imaging of the biological sample. In such cases, significant time (e.g., days, months, or years) can elapse between staining and/or imaging and performing analysis. In some embodiments, the array is adapted to facilitate biological analyte migration from the stained and/or imaged biological sample onto the array (e.g., using any of the materials or methods described herein). In some embodiments, a biological sample is per-meabilized before being contacted with an array. In some embodiments, the rate of permeabilization is slowed prior to contacting a biological sample with an array (e.g., to limit diffusion of analytes away from their original locations in the biological sample). In some embodiments, modulating the rate of permeabilization (e.g., modulating the activity of a permeabilization reagent) can occur by modulating a condition that the biological sample is exposed to (e.g., modulating temperature, pH, and/or light). In some embodi-ments, modulating the rate of permeabilization includes use of external stimuli (e.g., small molecules, enzymes, and/or activating reagents) to modulate the rate of permeabiliza-tion. For example, a permeabilization reagent can be pro-vided to a biological sample prior to contact with an array, which permeabilization reagent is inactive until a condition (e.g., temperature, pH, and/or light) is changed or an exter-nal stimulus (e.g., a small molecule, an enzyme, and/or an activating reagent) is provided.

Biological Samples

The methods of the disclosure, provided herein include spatial analysis of a biological analyte in a biological sample. In some embodiments, a biological sample is obtained from a subject for analysis using any of a variety of techniques including, but not limited to, biopsy, surgery, and laser capture microscopy (LCM), and generally includes cells and/or other biological material from the subject. In some embodiments, the biological sample is a tissue sample comprising cells. In some embodiments, the tissue sample comprising cells is a tissue section (e.g., tissue section obtained using a cryostat or microtome). In addition to the subjects described above, a biological sample can be obtained from non-mammalian organisms (e.g., a plants, an insect, an arachnid, a nematode (e.g., *Caenorhabditis elegans*), a fungi, an amphibian, or a fish (e.g., zebrafish)). In some embodiments, a biological sample can be obtained from a prokaryote such as a bacterium, e.g., *Escherichia coli, Staphylococci* or *Mycoplasma pneumoniae*; an archaea; a virus such as Hepatitis C virus or human immunodefi-ciency virus; or a viroid. In some embodiments, a biological sample can be obtained from a eukaryote, such as a patient derived organoid (PDO) or patient derived xenograft (PDX). In some embodiments, a biological sample can include organoids, a miniaturized and simplified version of an organ produced in vitro in three dimensions that shows realistic micro-anatomy. Organoids can be generated from one or more cells from a tissue, embryonic stem cells, and/or induced pluripotent stem cells, which can self-organize in three-dimensional culture owing to their self-renewal and differentiation capacities. In some embodiments, an organoid is a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, or a retinal organoid. Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy.

In some embodiments, a biological sample can include a single analyte of interest, or more than one analyte of interest. In some embodiments, more than one analyte type (e.g., nucleic acids and proteins) from a biological sample can be detected (e.g., simultaneously or sequentially) using any appropriate multiplexing technique, such as those described in Section (IV) of PCT Publication No. WO2020/176788 and/or U.S. Patent Application Publication No. 2020/0277663. In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of PCT Publication No. WO2020/176788 and/or Section (II)(b)(viii) U.S. Patent Application Publication No. 2020/0277663.

A variety of steps can be performed to prepare a biological sample for analysis. Except where indicated otherwise, preparative steps can generally be combined in any manner to appropriately prepare a particular sample for analysis.

In some embodiments, the biological sample, features, array, or combinations thereof can be protected from dehydration (e.g., drying, desiccation). In some embodiments, the biological sample, features, array, or combinations thereof, can be protected from evaporation. Methods of preserving and/or protecting biological samples, features, or arrays are known in the art. For example, in a non-limiting way, the biological sample, features, array, or combinations thereof can be covered by a reversible sealing agent. Any suitable reversible sealing agent can be used. Methods of reversible sealing are known in the art (See, e.g., WO 2019/104337, which is incorporated herein by reference). In a non-limiting way, suitable reversible sealing agents can include non-porous materials, membranes, lids, or oils (e.g., silicone oil, mineral oil). In further non-limiting examples, the biological sample, features, array, or combinations thereof can be preserved in an environmental chamber (e.g., hermetically sealed) and removed for additional rounds of spatial analysis at a later time.

Biological Analytes

The methods of the disclosure, provided herein include spatial analysis of a biological analyte in a biological sample.

For the purpose of this disclosure, an analyte of the disclosure will be understood to include any biological substance, structure, moiety, or component to be analyzed.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte can be an organelle (e.g., nuclei or mitochondria).

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). The RNA can be double-stranded RNA or single-stranded RNA. The RNA can be circular RNA. The RNA can be a bacterial rRNA (e.g., 16S rRNA or 23S rRNA).

Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample. In some embodiments, an analyte can be detected indirectly, such as through detection of an intermediate agent, for example, a ligation product or an analyte capture agent (e.g., an oligonucleotide-conjugated antibody), such as those described herein.

Additional examples of analytes include mRNA and cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a miRNA, a physical environmental (e.g., temperature change), or any other known perturbation agents.

Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, e.g., using a poly(T) containing primer. The generated cDNA can then be barcoded using a capture probe, featuring a barcode sequence (and optionally, a UMI sequence) that hybridizes with at least a portion of the generated cDNA. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, and PCT Patent Publication Nos. WO 2021/247568 and WO 2021/247543. V(D)J analysis can also be completed with the use of one or more labelling agents that bind to particular surface features of immune cells and associated with barcode sequences. The one or more labelling agents can include an MHC or MHC multimer.

As described above, the analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the analyte (e.g., a sequence that can hybridize to the CRISPR RNA (crRNA), single guide RNA (sgRNA), or an adapter sequence engineered into a crRNA or sgRNA).

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the Applicant reserves the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Additional embodiments are disclosed in further detail in the following examples, which are provided by way of illustration and are not in any way intended to limit the scope of this disclosure or the claims.

EXAMPLES

Example 1

HRP-Mediated Surface Gelation on Microspheres

This Example describes an exemplary process of HRP-mediated surface gelation of microspheres. An aqueous monomer mixture was prepared with acrylamide, 5' acrydite oligonucleotide, N-(3-aminopropyl)methylacrylamide HCl, and sodium formate. Polymerization of linear polyacrylamide chains was then thermally initiated with VA-044. The polymer was dialyzed three times to recover polyacrylamide chains of the desired length. Next, the polyacrylamide was phenol functionalized and the resultant functionalized polymer was dialyzed three times.

HRP-conjugated microspheres were suspended in the aqueous solution containing the phenol functionalized polyacrylamide polymer, and the solution was thoroughly mixed at room temperature on a shaker. The microsphere/polymer solution was then transferred to a 4° C. shaker, hydrogen peroxide was added, and the solution was thoroughly mixed. In the presence of hydrogen peroxide and HRP, the phenolic groups in the polymer crosslinked to form a hydrogel. Because the HRP was confined to the surface of the microsphere, a hydrogel coating was formed on the microsphere surface. The resultant amine modified hydrogel-coated microspheres could be functionalized with barcodes and arrayed with EDC-coupling on N-oxysuccinmide glass slide.

The thickness and porosity of the hydrogel polymer coating can be adjusted by tuning the polymer chemistry and concentration of bound HRP on the microsphere surface Additional functionality could be added to the polyacrylamide chains as desired.

Example 2

Preparation of Hydrogel-Coated Microspheres Using Particle Templated Emulsification This Example describes the preparation hydrogel coated microspheres using Particle Templated Emulsification (PTE). First a phenolic polymer for hydrogel coating was prepared as follows. An aqueous monomer mixture was prepared with acrylamide, 5' acrydite oligonucleotide, and sodium formate. Polymerization of linear polyacrylamide chains was then thermally initiated with VA-044. The polymer was dialyzed three times to recover polyacrylamide chains of the desired length. Next, the polyacrylamide was phenol functionalized and the resultant functionalized polymer was dialyzed three times.

Microspheres were suspended in an aqueous solution containing the phenol functionalized polyacrylamide polymer, Horseradish Peroxidase (HRP), and Triton X-100 surfactant. The solution was thoroughly mixed. Then, partitioning oil was added and the sample was vortexed a minimum of 30 seconds to partition the microspheres with the hydrogel polymer in the immiscible oil using Particle templated emulsification (PTE). PTE uses particles such as microspheres, oil, and a standard benchtop vortexer to rapidly emulsify large volumes into monodisperse droplets. Once the microspheres were encapsulated, hydrogen peroxide was added. The hydrogen peroxide was delivered to the aqueous partitions via micelle mediated transport. In the presence of hydrogen peroxide and HRP, the phenolic groups in the polymer crosslinked to form a hydrogel coating around the microsphere.

Each round of PTE generated a hydrogel coating of a certain thickness n. If and when desirable to have a thicker hydrogel coating than n, then the process can be iteratively repeated to generate successively thicker coatings until desired thickness is achieved. In addition, the surface of the microsphere could be modified before PTE by a number of standard techniques including silane deposition and polymer adsorption.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A hydrogel-coated feature comprising:
(a) a solid particle; and
(b) a hydrogel encapsulating the solid particle, wherein the hydrogel comprises a crosslinked polymer and a plurality of moieties.

2. The hydrogel-coated feature of claim 1, wherein each moiety of the plurality of moieties comprises an oligonucleotide, wherein the oligonucleotide is configured to hybridize to a capture probe.

3. The hydrogel-coated feature of claim 1, wherein each moiety of the plurality of moieties comprises an organic functional group, wherein the organic functional group is capable of attachment to a capture probe.

4. The hydrogel-coated feature of claim 3, wherein the organic functional group is an amine group.

5. The hydrogel-coated feature of claim 1, wherein the hydrogel comprises an acrylamide copolymer.

6. The hydrogel-coated feature of claim 5, wherein the acrylamide copolymer is prepared from (i) acrylamide and 3-aminopropyl methacrylamide monomers or (ii) acrylamide, 3-aminopropyl methacrylamide, and 5' acrydite oligonucleotide monomers.

7. The hydrogel-coated feature of claim 6, wherein the acrylamide copolymer is prepared (i) in the presence of sodium formate, (ii) in the presence of a polymerization initiator or (iii) in the presence of sodium formate and a polymerization initiator.

8. The hydrogel-coated feature of claim 3, wherein the organic functional group is phenol.

9. The hydrogel-coated feature of claim 1, wherein the solid particle is a microsphere, optionally wherein the microsphere has a diameter of about 1 micrometer to about 100 micrometers.

10. The hydrogel-coated feature of claim 1, wherein the hydrogel-coated feature comprises a plurality of capture probes and wherein each capture probe is attached to a moiety of the plurality of moieties within the hydrogel.

11. The hydrogel-coated feature of claim 10, wherein capture probe comprises a barcode sequence and a capture domain.

12. The hydrogel-coated feature of claim 11, wherein the capture domain comprises a poly(T) sequence, a random sequence, a gene specific sequence, or a degenerate sequence.

13. The hydrogel-coated feature of claim 10, wherein the capture probe further comprises a unique molecular identifier (UMI) and/or a functional domain.

14. The hydrogel-coated feature of claim 10, wherein the feature comprises the plurality of capture probes at an average density of about 1,000 to about 100,000 capture probes per micrometer$^2$.

15. A substrate comprising a plurality of the hydrogel-coated features of claim 1, wherein the hydrogel-coated features are immobilized on the substrate.

16. The substrate of claim 15, wherein the hydrogel-coated features are spatially ordered in an array and wherein each hydrogel-coated feature of the plurality of the hydrogel-coated features is associated with a unique spatial location on the array.

17. The substrate of claim 15, wherein the substrate comprises glass, silicon dioxide or a silicon wafer.

18. A method for spatial analysis of a biological analyte in a biological sample, comprising:
(a) providing a substrate comprising hydrogel-coated features of claim 1;
(b) contacting the substrate with the biological sample under conditions sufficient for at least one biological analyte of the biological sample to hybridize to a capture probe on at least one hydrogel-coated feature; and
(c) determining (i) all or a part of the sequence of the biological analyte hybridized to the capture probe, or a complement thereof, and (ii) the spatial barcode, or a complement thereof, and using the determined sequence of (i) and (ii) to identify the location of the biological analyte in the biological sample.

19. A method of preparing a hydrogel-coated feature, comprising:
(a) providing a solid particle; and
(b) encapsulating the solid particle with a hydrogel comprising a crosslinked polymer and a plurality of a moieties.

20. A method for preparing a plurality of hydrogel-coated features comprising:
(a) suspending a plurality of features in an aqueous solution comprising a linear polymer, a surfactant, and an enzyme, thereby forming a suspension comprising the plurality of features;
(b) adding an oil to the suspension and emulsifying the suspension into a plurality of droplets, wherein a droplet of the plurality of droplets comprises a feature of the plurality of features coated with the linear polymer and the enzyme;
(c) contacting the plurality of droplets with a substrate for the enzyme, wherein the enzyme mediates crosslinking of the linear polymer to form a hydrogel on a feature of the plurality of features, thereby forming a plurality of hydrogel-coated features.

21. A method of immobilizing a capture probe on a feature, comprising:
(a) encapsulating a solid particle with a hydrogel comprising a crosslinked polymer, and
(b) attaching the capture probe to a moiety within the hydrogel.

22. A method for preparing a plurality of hydrogel-coated features comprising:

(a) suspending a plurality of features in an aqueous solution comprising a polymerizable monomer and a surfactant, thereby forming a suspension comprising the plurality of features;

(b) adding a partitioning oil to the suspension and emulsifying the suspension into a plurality of droplets, wherein a droplet of the plurality of droplets comprises a feature of the plurality of features coated with the monomer;

(c) contacting the plurality of droplets with a polymerization agent such that the monomer coating a feature of the plurality of features is polymerized to form a plurality of hydrogel-coated features.

\* \* \* \* \*